US008324173B2

(12) United States Patent
Chauvier et al.

(10) Patent No.: US 8,324,173 B2
(45) Date of Patent: Dec. 4, 2012

(54) PEPTIDES USEFUL AS DUAL CASPASE-2/-6 INHIBITORS AND THEIR BIOLOGICAL APPLICATIONS

(75) Inventors: David Chauvier, Limeil-Brevannes (FR); Richard Casimir, Noisiel (FR); Johan Hoebeke, Kessel-Lo (BE)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 13/186,065

(22) Filed: Jul. 19, 2011

(65) Prior Publication Data

US 2012/0021990 A1    Jan. 26, 2012

Related U.S. Application Data

(62) Division of application No. 11/791,469, filed as application No. PCT/EP2005/013976 on Nov. 24, 2005, now abandoned.

(60) Provisional application No. 60/630,249, filed on Nov. 24, 2004.

(51) Int. Cl.
*A61K 38/08* (2006.01)
*A61P 25/14* (2006.01)

(52) U.S. Cl. ...................... 514/21.8; 514/17.8

(58) Field of Classification Search .................. None
See application file for complete search history.

(56) References Cited

U.S. PATENT DOCUMENTS

| 6,248,904 | B1 * | 6/2001 | Zhang et al. | .................. 549/227 |
| 6,583,275 | B1 | 6/2003 | Doucette-Stamm et al. | |
| 2003/0233675 | A1 | 12/2003 | Cao et al. | |
| 2004/0031072 | A1 | 2/2004 | La Rosa et al. | |
| 2004/0086500 | A1 * | 5/2004 | Bahr et al. | .................. 424/94.5 |
| 2004/0123343 | A1 | 6/2004 | La Rosa et al. | |
| 2007/0172489 | A1 | 7/2007 | Ludwig et al. | |

FOREIGN PATENT DOCUMENTS

| JP | 7-505772 | 6/1995 |
| JP | 2000-504331 | 4/2000 |
| JP | 2004-81178 | 3/2004 |
| JP | 2004-509120 | 3/2004 |
| WO | WO 90/12882 | 11/1990 |
| WO | WO 93/20206 | 10/1993 |
| WO | WO 96/01893 | 1/1996 |
| WO | WO 96/40893 | 12/1996 |
| WO | WO 97/27220 | 7/1997 |
| WO | WO 97/45535 | 12/1997 |
| WO | WO 99/11784 | 3/1999 |
| WO | WO 00/56752 | 9/2000 |
| WO | WO 01/85743 | 11/2001 |
| WO | WO 0185955 | * 11/2001 |
| WO | WO 02/22611 | 3/2002 |
| WO | WO 02/099122 | 12/2002 |
| WO | WO 03/020953 | 3/2003 |
| WO | WO 03/066652 | 8/2003 |
| WO | WO 2004/024064 | 3/2004 |
| WO | WO 2004/085682 | 10/2004 |
| WO | WO 2004/103389 | 12/2004 |
| WO | WO 2005/105829 | 11/2005 |

OTHER PUBLICATIONS

Dictionary entry for carboxy group (retrieved from http://encyclopedia2.thefreedictionary.com/carboxy+group on Mar. 13, 2012, 2 pages).*
Wang et al ('Purification of an interleukin-1B converting enzyme-related cysteine protease that cleaves sterol regulatory element-binding proteins between the leucine zipper and transmembrane domains' JBC v270 Jul. 28, 1995 pp. 18044-18050).*
Curing Epilepsy Sep. 2007 National Institutes of Health retrieved from http://www.ninds.nih.gov/disorders/epilepsy/Curing_Epilepsy_Brochure.pdf on Oct. 12, 2010, 21 pages.
Sepsis retrieved from http://kidshealth.org/parent/pregnancy_center/newborn_health_conditions/sepsis.html# on Oct. 12, 2010 4 pages.
Glaucoma:frequently asked questions retrieved from http://www.allaboutvision.com/faq/glaucoma.htm on Oct. 12, 2010 2 pages.
Gregoli et al, "Function of caspases in regulating apoptosis caused by erythropoietin deprivation in erythroid progenitors", Journal of Cellular Physiology, Feb. 1999, vol. 178, No. 2, pp. 133-143.
International Search Report mailed Mar. 19, 2008, issued in connection with PCT/EP2005/013976.
Japanese Office Action dated Aug. 9, 2011, issued in corresponding Japanese Application No. 541884/07.
Talaniant et al, "Substrate Specificities of Caspase Family Proteases", Journal of Biological Chemistry, 1997, vol. 272, pp. 9677-9682.
Schweizer et al, "Crystal Structure of Caspase-2, Apical Initiator of the Intrinsic Apoptotic Pathway", Journal of Biological Chemistry, 2003, vol. 278, pp. 42441-42447.

* cited by examiner

*Primary Examiner* — Cecilia J Tsang
*Assistant Examiner* — Ronald Niebauer
(74) *Attorney, Agent, or Firm* — Nixon & Vanderhye P.C.

(57) ABSTRACT

The present disclosure relates to peptides having a core sequence as described herein as well as application of the disclosed technology as inhibitors of caspase-2 and/or -6 activity.

4 Claims, 10 Drawing Sheets

SEQUENCE LISTING

```
<160> NUMBER OF SEQ ID NOS: 29

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Asp Glu Ala Asp
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Asp Glu Gly Asp
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Asp Glu Gly Asp
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Asp Glu Ser Asp
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Leu Asp Glu Lys Asp
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Asp Glu Ser Asp
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Asp Glu Ala Asp
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Asp Val Ala Asp
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Asp Val Ala Asp
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Asp Val Ala Asp
1               5

<210> SEQ ID NO 11
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 11

Trp Glu His Asp
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 12

Asp Glu Xaa Asp
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Val
<220> FEATURE:
<221> NAME/KEY: MOD_RES
<222> LOCATION: (3)..(3)
<223> OTHER INFORMATION: Any amino acid

<400> SEQUENCE: 13

Xaa Glu Xaa Asp
1

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Asp Glu Ser Asp
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Asp Glu Ala Asp
1               5

<210> SEQ ID NO 16
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Asp Glu Gly Asp
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Asp Glu Gly Asp
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Asp Glu Ser Asp
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Asp Glu Lys Asp
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Asp Glu Ser Asp
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Asp Glu Ala Asp
1               5
```

```
<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Asp Glu Gly Asp
1               5

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Val Ala Asp
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Glu Val Asp
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Glu Ile Asp
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Glu Thr Asp
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 27

Leu Glu His Asp
1

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Asp Val Glu Ala Asp
1               5

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Glu Pro Asp
1
```

PEPTIDES USEFUL AS DUAL CASPASE-2/-6 INHIBITORS AND THEIR BIOLOGICAL APPLICATIONS

The present application is a divisional of application Ser. No. 11/791,469, filed Dec. 10, 2007 (abandoned), which published as US-2009-0042805-A1 on Feb. 12, 2009, and is the U.S. National phase of international application no. PCT/EP2005/013976 filed Nov. 24, 2005, which was published as WO2006/056487 on Jun. 1, 2006, which designated the U.S. and which claims benefit of U.S. Provisional Application No. 60/630,249, filed Nov. 24, 2004, the entire content of which is hereby incorporated by reference.

The invention relates to new peptides useful as dual caspase-2/caspase-6 inhibitors. It also relates to the biological and their applications thereof.

All caspases (cysteine aspartate proteases) show a high degree of specificity with an absolute requirement for cleavage after an aspartic acid residue and a recognition sequence of normally four consecutive amino acids N-terminal to the cleavage site. Using a combinatorial approach they have been classified into three distinct specificity groups: group I (caspases-1, -4, -5) with preference for Trp-Glu-His-Asp (SEQ ID NO:11), group II (caspases-2, -3, -7) with preference for Asp-Glu-X-Asp (SEQ ID NO:12) and group III (caspases-6, -8, -9 and -10) with a preference for (Leu/Val)-Glu-X-Asp (SEQ ID NO:13). This characteristic specificity is crucial to the apoptotic process as it involves cleavage of a particular group of proteins in an ordered manner rather than indiscriminate proteolysis. Based on their role in cellular context, caspases may be considered as executionner (direct cleavage of specific downstream protein substrates playing role in cell architecture, cell cycle regulation, or signalisation pathway) or initiator caspase (acting an as upstream regulator of apoptosis pathway). Given their pivotal role in the regulation of apoptosis, caspases are important therapeutic targets. A number of neurological diseases are connected to the caspase apoptotic pathway and some small caspase inhibitors have been shown to block the effects of neuronal cell death. A controlled activation of caspases, as desirable for cancer and neurodegenerative diseases treatment, is more difficult to achieve. A possible strategy could involve the design of compounds that specifically inhibit an essential caspase in a given pathological setting rather all caspases.

Caspase-2 was discovered as the first mammalian apoptotic caspase. Recent studies revealed that caspase-2 is engaged as initiator in both the extrinsic and the intrinsic pathways of apoptosis in non-neuronal cells (Lassus et al., 2002). Additionally, caspase-2 acts both as a default initiator and a default executioner caspase. Recently, the inventors demonstrated that caspase-2 initiates serum deprived-induced apoptosis in primary cortical neurons, an in vitro model that mimics partially in vivo cerebral ischemia (Chauvier et al., 2005). Caspase-2 may also be able to cleave huntingtin thus possibly participating in Huntington pathogenesis. Its substrate specificity is not fully understood, and only two pentapeptidic VDVAD (SEQ ID NO:9)- and LDESD (SEQ ID NO:14)-based inhibitors are available.

Caspase-6 is implicated in neuronal (developmental) cell death and is rather an executioner caspase than initiator. There are at least four pathological conditions in which caspase-6 is known to be activated: in dystrophic neurites and neurofibrillary tangles of Alzheimer disease; during human fetal and adult cerebral ischemia (Guo et al., 2004); in rat kainic acid seizure model suggesting a role for eliptogenesis and epilepsy; in anoikis of the gastrointestinal lining epithelial cells. Caspase-6 substrate specificity is poorly known. A tetrapeptidic VEI(or H)D(SEQ ID NO:13)-based inhibitor is available, but, no pentapeptidic-based inhibitors are available for caspase-6

I/FIELD OF THE INVENTION

The invention is in the field of molecular modeling, medicinal biology and chemistry and relates to novel compounds, and pharmaceutical compositions comprising said compounds, that inhibit pro-apoptotic caspase-2 (Nedd-2; Ich-1) and/or inhibit pro-apoptotic caspase-6 (Mch2), and are useful to treat diseases and injuries where caspase-2 activity and/or caspase-6 is implicated.

The invention relates to new peptides having a core sequence selected in the group comprising:

```
SEQ ID NO: 1: VDEAD
SEQ ID NO: 2: LDEGD
SEQ ID NO: 3: VDEGD
SEQ ID NO: 4: VDESD
SEQ ID NO: 5: LDEKD
SEQ ID NO: 6: FDESD
SEQ ID NO: 7: LDEAD.
```

Said peptides advantageously have a N-terminal and/or C-terminal protecting group. According to one embodiment of the invention, the peptides have a N-terminal protecting group M which represents A-$(CH_2)_{n1}$, wherein n1=0 to 20

M is H when n1=0,

A is a $C_1$-$C_{20}$ alkyl, one or several condensed cycles and/or heterocycles, A, when different from H, and when n1 is above 2, being saturated or unsaturated and optionally substituted by one or several groups such as H, $OH_1OR_a$, $(CH_2)_piOH_1(CH_2)niO$-$R_a$, COOH, $COOR_a$, $(CH_2)_niCOOH$, $(CH_2)_{n1}COOR_a$, $C_1$-$C_3$ alkyl or cycloalkyl, $(CH_2)$ni-alkyl, CO—NH-alkyl, Ar, $(CH_2)_n$i-Ar, CO—NH—$Ar_1$ halogen, $CF_3$, $SO_3H$, $(CH_2)_x$$PO_3H_2$, $B(OH)_2$, $NO_2$, $SO_2NH_2$, $SO_2NHR_3$, with x=0, 1 or 2, $R_a$ being a $C_1$-$C_3$ alkyl and Ar being an optionally substituted aryl or heteroaryl group, or A is one or several aminoacid residues or A represents a chromophore, a fluorescent, luminescent, absorbing (UV to near IR) group, a radioisotope, metallic particles such as used in electronic microscopy, colorimetric group, biolin/stepravidin/neutravidin labeling systems, or analogues.

According to another embodiment, eventually used in combination with the above disclosed embodiment, the peptides of the invention have a carbony group with X is H or a carboxy protecting group selected in the group comprising $OR_b$, $NHR_b$, $SR_b$, $CH_2OR_b$, $CH_2NHR_b$, $CH_2SR_b$, $CH_2OR_b$ and $CH_2Y$, in which $R_b$=acyl, alkyl, substituted alkyl, aryl, heteroaryl, substituted aryl or heteroaryl, optionally condensed with one or several cycles and/or heterocycles, a C1-C20 substituted or unsubstituted aliphatic, aralkyl carbocyclic alkyl carbocyclic, or heterocyclic group, optionally condesed with one or several aromatic or not cycles and Y is an halogen atom (F, Cl, Br or I) or $NO_2$, or X represents a chromophore, a fluorescent, luminescent, absorbing (UV to near IR) group, a radioisotope, metallic particles such as used in electronic microscopy, a colorimetric group, biotin/streptavidin/neutravid in labeling systems, or analogues.

As illustrated by the examples, the above disclosed peptides particularly have inhibitor properties with respect to caspase-2 and/or -6 activity.

The invention thus also relates to their use as inhibitors for preventing or blocking caspase-2 activity in cell death, particularly in neurons, neuronal cells, or in non-neuronal cells.

Moreover, the peptides of the invention have a high innocuity. No toxicity is observed at 100 mg/kg by iv or ip injection in adult Swiss mice.

Said properties are advantageously used in pharmaceutical compositions.

The invention thus also relates to pharmaceutical compositions comprising a therapeutically effective amount of at least one peptide or caspase-2 and/or -6 inhibitor such as above defined in association with a pharmaceutically acceptable carrier.

Said compositions pharmaceutical are under forms appropriate for administration by oral, nasal, local (subcutaneous, intracerebroventricular, intracerebral implantation of material impregnated with compounds or pharmaceutical compositions, intracerebral implantation of instrumentation for mechanical delivery, for example) or systemic (for example: intraperitoneal, intravenous ... ) administration to reduce cell death.

The compositions of the invention are administered at dosis appropriate for the pathology to be treated and the age of the patient. Said doses are in particular of $10^{-9}$ mg to 100 g/Kg, especially 0.1 to 10 mg/kg.

Such doses are efficient for treating global ischemia of newborn (term birth), child, adult.

They are administered by the oral route or by ip, iv or subcutaneous injection (1 or several).

Said pharmaceutical compositions are particularly useful for the treatment of
- pathological situation including hypoxia-ischemia (H-I) H-I (ischemia with or without hypoxia/hypoglycaemia) injuries and stroke-like situations (cerebral, renal, cardiac failure, for example);
- pathological situation including cerebral hypoxia-ischemia (H-I) (ischemia with or without hypoxia/hypoglycaemia) injuries and stroke-like situations (cerebral, renal, cardiac failure, for example);
- neuronal death particularly in global or focal H-I (ischemia with or without hypoxia/hypoglycaemia) injuries and stroke-like situations (cerebral, renal, cardiac failure, for example);
- neuronal death particularly in adult, fetal or perinatal H-I (ischemia with or without hypoxia/hypoglycaemia) injuries and stroke-like situations (cerebral, renal, cardiac failure, for example);
- neuronal death particularly in transient or permanent H-I (ischemia with or without hypoxia/hypoglycaemia) injuries and stroke-like situations (cerebral, renal, cardiac failure, for example);
- neuronal death particularly H-I (ischemia with or without hypoxia/hypoglycaemia) injuries and stroke-like situations brain injuries with or without reperfusion situation (cerebral, renal, cardiac failure, for example);
- neuronal death particularly in Middle Cerebral Artery Occlusion (MCAO) in adult, fetal or perinatal H-I.
- neuronal death particularly when at least one or more of the following pathological events are combined: global or focal, transient or permanent, adult or fetal or perinatal H-I (ischemia with or without hypoxia/hypoglycaemia) at cerebral level, or at the level of whole body) with or without reperfusion;
- neuronal death particularly when at least one or more of the following brain injury;
- neuronal death particularly when at least one or more of the following perinatal brain injury.

More precisely:
(a) The invention relates to the molecular docking of pentapeptides-caspase-2 protein complexes, that allow to (i) identify amino acid residues that are needed to provide contacts with caspase-2 and (ii) define the nature of interactions between these sequences and caspase-2
(b) The invention relates to the obtention of new pentapeptidic sequences/based-inhibitors that induce formation of reversible or irreversible complexes with caspase-2 (i.e., with lower minimal energy), thus resulting in experimental inhibition of caspase-2 activity.
(c) The invention relates to the obtention of the first pentapeptidic sequences/pentapeptidic-based compounds that both inhibit caspase-2 and caspase-6 activity, but not other caspases or proteases (calpains, granzyme B)
(d) The invention relates to the obtention of the first pentapeptidic sequences or pentapeptidic-based compounds that lead to caspase-6 inhibition
(e) The invention relates to the obtention of the first pentapeptidic sequences or pentapeptidic-based compounds that inhibits both caspase-2 and caspase-6 activity with similar dose range.
(f) Rational design of new caspase-2 inhibitors can be achieved by combining molecular docking and functional cleavage in vitro assays.
(g) In a non restrictive embodiment, these sequences can be combined to methylmalonyl derivatives, quinolinyl derivatives in their N-terminus extremity. In a non restrictive embodiment, nucleofuges like 2,6-difluorophenyl ester, 2,6-difluorophenoxy, 2-bromobenzoyloxy, fluorine can be added in carboxy terminal position. In a non restrictive embodiment, the amino acid side chains can comprise protecting groups, such as methyl group, to improve cellular permeability and retention. Based on previous data, such pentapeptidic sequences/ related compounds are accurate templates for inhibition of in vitro ischemic neuronal cell death (especially apoptosis, Chauvier et al., 2005) and in in vivo pathological situations including cerebral (hypoxia-)ischemia injuries (focal transient perinatal H-I or MCAO (Middle Cerebral Artery Occlusion); FR patent application 03 06 190 and WO 2004/103389; in the name of Theraptosis SA.
(h) The invention relates to the discovery that new caspase-2 inhibitors prevents or decreases cerebral cell death in in vivo pathological situations including cerebral global adult ischemia following blood flow reduction/hypoxia during cardiac arrest or cardiovascular injuries.
(i) The invention relates to new applications for new caspase inhibitors including local (intracerebroventricular, intrahippocampal, for example) delivery or systemic (intraperitoneal, intravenous . . . ) administration to reduce cerebral cell death during pathological situations in which blood flow and oxygen pressure are disturbed, i.e. cerebral (transient or permanent) focal or global ischemia.
(j) The invention also relates to method of treatment of pathologies with cell death, particularly ischemia and stroke injuries, comprising the administration of a therapeutically effective dose of a pharmaceutical composition such as above defined.

(k) The pharmaceutical compositions comprising an effective amount of the peptides according to the invention are particularly useful for preventing, reducing and treating pathologies with cell death, particularly in H-I injuries and stroke-like situations brain injuries: for example, global or focal, transient or permanent, adult, fetal, perinatal H-I (ischemia with or without hypoxia/hypoglycaemia) with origin at cerebral or heart level, with or without reperfusion, or MCAO (Middle Cerebral Artery Occlusion).

BRIEF DESCRIPTION OF THE FIGURES

Precised characteristics and advantages of the invention are given in the following data and with reference to FIGS. 1 to 17 (sequences of the figures correspond to the following sequence identifiers: SEQ ID NO:1—VDEAD; SEQ ID NO:2—LDEGD; SEQ ID NO:4—VDESD; SEQ ID NO:5—LDEKD; SEQ ID NO:6—FDESD; SEQ ID NO:7—LDEAD; SEQ ID NO:9—VDVAD; SEQ ID NO:14—LDESD; SEQ ID NO:27 LEHD), which represent, respectively.

II/RATIONAL DESIGN OF SEQUENCES AND INHIBITORS OF CASPASE-2

II-1/Methodology

The caspase-2—inhibitor complex corresponded to structure 1pyo of the Protein Data Bank (Schweizer et al., 2003). All models were studied in an uncharged form and at a dielectric constant of 1. The inhibitor was manually modified by the Biopolymer module of Accelrys (San Diego, Calif.). The enzyme atoms were fixed and the inhibitor minimalized with the Discover module using 2000 steps of conjugated gradient until the RMS was <0.0001 Kcal/mol·Å. Non covalent energy values (Van der Waals and Coulombic) were calculated with the InsightII module.

II-2/Results and Discussions

Figure 1:
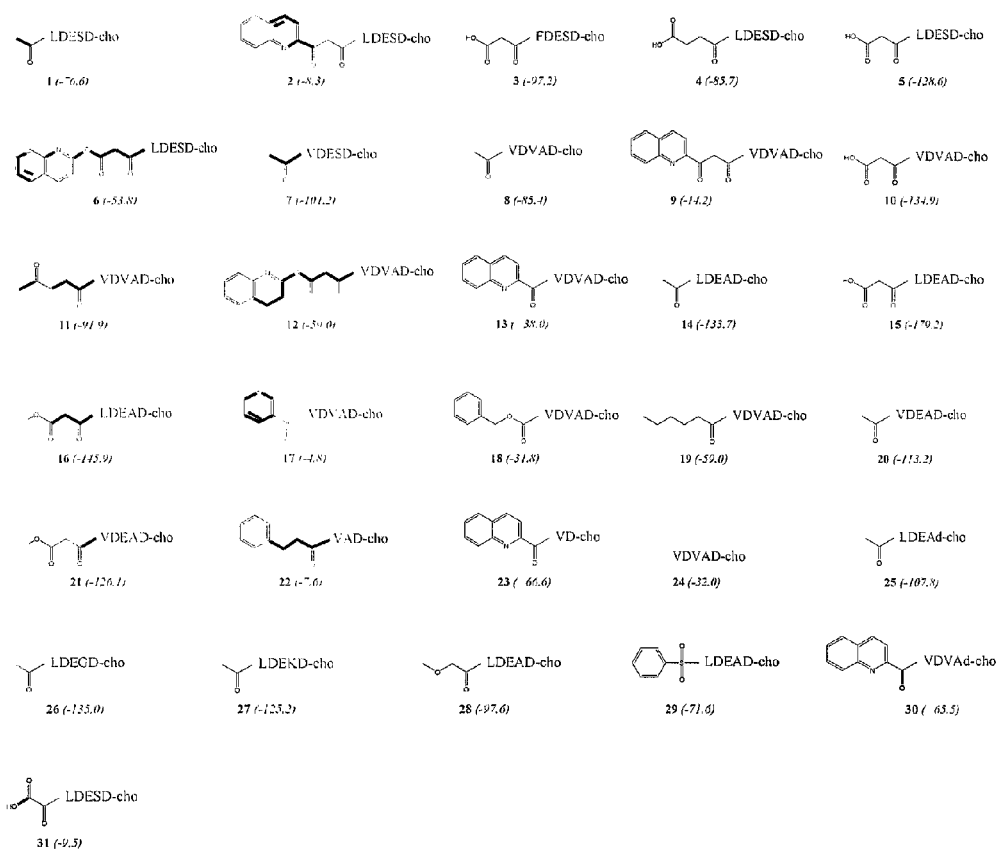
FIG. 1: the structure of caspase-2 inhibitors of the invention.

FIG. 1 shows a series of compounds that was studied by molecular modeling using the above described methodology. The potency of these compounds to inhibit the caspase-2 enzyme is characterized by the minimal energy ($E_{min}$Kcal/mol) of the corresponding enzyme—inhibitor complex (FIG. 1). This energy is composed of two components:

(i) electric or coulombic component ($E_{coulombic}$) resulting from hydrogen bonding and salt bridges between the inhibitor and the enzyme residues (ii) repulsion—attraction component ($E_{Van\ der\ Waals}$) resulting from Van der Waals interactions between the inhibitor and the enzyme.

Figure 2:
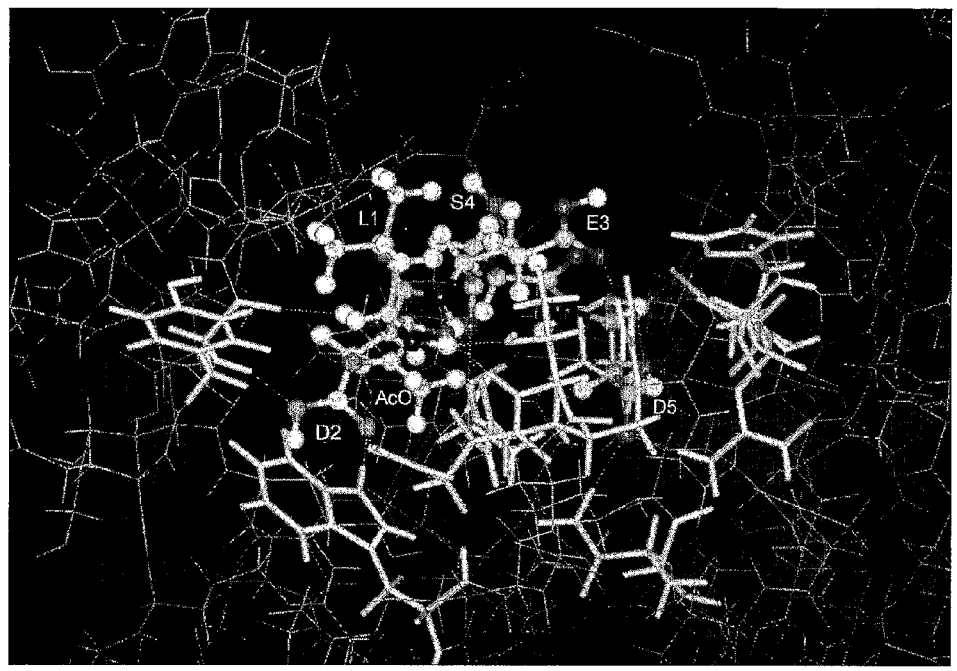
FIG. 2: compound 1 (Ac-LDESD(SEQ ID NO:14)-cho) in the active site of caspase-2

FIG. 2 shows the reference molecule Ac-LDESD(SEQ ID NO:14)-cho 1 in the active site of caspase-2. As shown, the atoms of this pentapeptide are represented as follow (a) green=carbon, (b) white=hydrogen, (c) blue=nitrogen, (d) red=oxygen. The electric interactions (hydrogen bonds and salts bridges) between this inhibitor and the caspase-2 enzyme are represented by the dashed, green lines. In this Figure, the enzyme's residues which interact with the inhibitor 1 are represented in yellow and those which do not interact with the inhibitor are shown in magenta. The inhibitor's residues are represented by their one-letter code followed by a number indicating their position in the inhibitor sequence. The protection of the amino group on the first residue is also indicated. For clarity reasons, the Van der Waals interactions are not shown in FIG. 1. The same logic was used throughout the text for representing the complexes formed between other newly designed pentapeptidic inhibitors and the caspase-2 enzyme.

Figure 3:
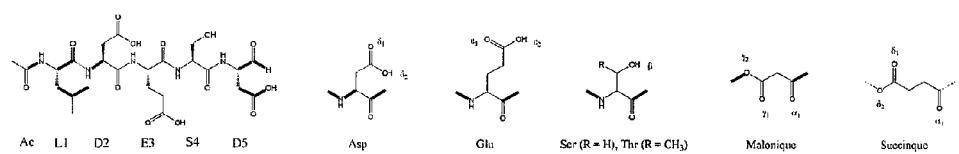
FIG. 3: the structure of Ac-LDESD(SEQ ID NO:14)-cho 1 and some residues and functional groups.

As shown in FIG. 2, the hydrogen bonds and salt bridges that stabilize the complex between Ac-LDESD(SEQ ID NO:14)-cho 1 and the caspase-2 active site are the followings: L1 (NH)-T B233 (OH), L1 (CO)-T B233 (NH), D2 (NH)—Y B273 (CO), D2 (O$\delta_2$)-Y B273 (NH), D2 (O$\delta_1$)-W B238 (indole) and N B232 (NH$_2$), E3 (NH)—R B231 (CO), E3 (O$\delta_1$)-R B231 (guanidine, salt bridge), E3 (CO)—R B231 (NH), D5 (NH)-A B229 (CO), D5 (O$\delta_1$)-Q A153 (NH$_2$) and R A54 (NH$_2$), D5 (O$\delta_2$)-R B231 (guanidine, salt bridge) and R A54 (guanidine, salt bridge), D5 (CO)—C A155 (NH) and H A112 (imidazole) and G A113 (NH). The nomenclature used for designing the residues, the oxygen atoms of the residue's side chains and the amino protection of the first residue are indicated in FIG. 3.

The ability of each of the compounds studied to inhibit the caspase-2 enzyme was compared to that of the reference pentapeptide Ac-LDESD(SEQ ID NO:14)-cho $I_1$ which showed a minimal energy ($E_{min}$) of −76.6 Kcal/mol in the used model.

The following conclusions can thus be drawn from the inventors' work.

II-2.1/Residue Substitutions

Figure 4:
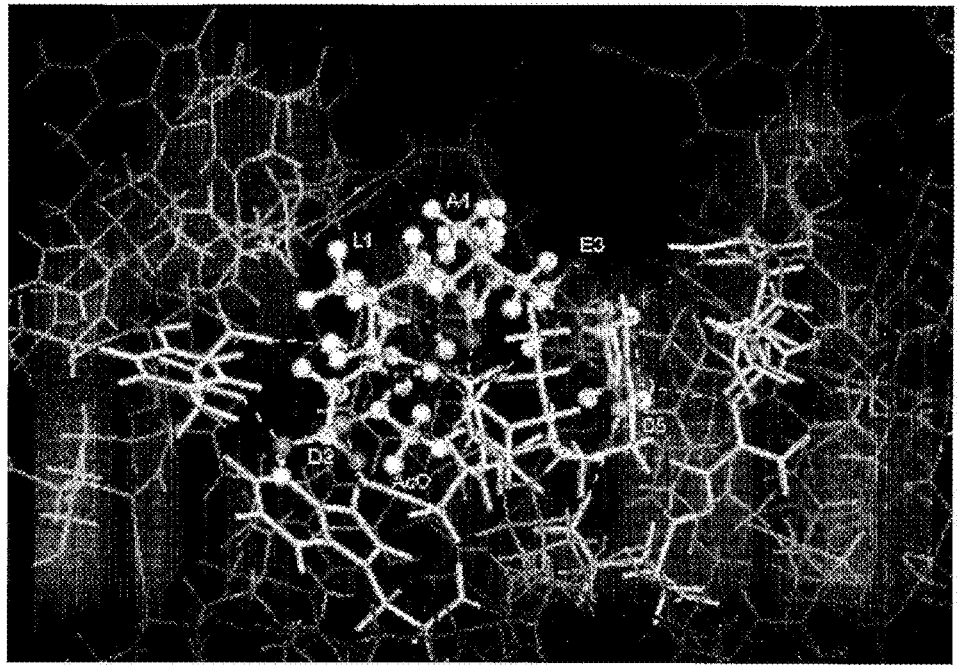
FIG. 4: the superposition of Ac-LDESD(SEQ ID NO:14)-cho 1 and Ac-LDEAD(SEQ ID NO:7)-cho 14 in the active site of caspase-2.

The substitution of L1 by V1 (Ac-VDESD(SEQ ID NO:4)-cho 7, $E_{min}$=−101.2 Kcal/mol) allows a better stability of the inhibitor-caspase-2 complex. The potency of the inhibitor was even greater when S4 was replaced by (i) K4 (Ac-LDEKD(SEQ ID NO:5)-cho 27, $E_{min}$=−101.2 Kcal/mol), (ii) A4 (Ac-LDEAD(SEQ ID NO:7)-cho, compound 14, $E_{min}$=−133.7 Kcal/mol), or (iii) G4 (Ac-LDEGD(SEQ ID NO:2)-cho, compound 26, $E_{min}$=−135.0 kcal/mole). These observations thus showed that compounds 7, 14, 26 and 27 are better inhibitors of caspase-2 than the reference compound 1 (Ac-LDESD(SEQ ID NO:14)-cho). FIG. 4 shows the superposition of compounds I and 14 (Ac-LDEAD(SEQ ID NO:7)-cho) in the active site caspase-2.

The comparison of compound 20 ($E_{min}$=−113.2 Kcal/mol, substitution of L1 by V1 and S4 by A4, Ac-VDEAD(SEQ ID NO:1)-cho) to compound 7 ($E_{min}$=−101.2 Kcal/mol, substitution of L1 by V1, Ac-VDESD(SEQ ID NO. 4)-cho) indicates that in position 4, alanine (A4) allows a better stabilization of the enzyme-inhibitor complex than serine (S4).

The results obtained with compounds 8 $E_{min}$ E=−85.4 kcal/mole, substitution of L1 by V1, E3 by V3, and S4 by A4, Ac-VDVAD(SEQ ID NO:9)-cho) and 20 ($E_{min}$=−113.2 Kcal/mol, substitution of L1 by V1, and of S4 by A4, Ac-VDESD (SEQ ID NO:4)-cho) shows that glutamic acid (E3) allows a better stabilization of caspase-2 than valine (V3) at position 3.

Moreover, the comparison of compound 3 ($E_{min}$=−97.2 Kcal/mol, substitution of L1 by F1, Ac-FDESD(SEQ ID NO:6)-cho) to 5 ($E_{min}$=−128.6 Kcal/mol, Ac-LDESD(SEQ ID NO:14)-cho) indicates that at position 1, leucine (L1) allows a better stabilization of the enzyme-inhibitor complex than the phenylalanine (F1) residue.

Furthermore, the substitution of D2 and/or D5 by other amino acids showed a great increase in the minimal energy ($E_{min}$) of the inhibitor—caspase-2 complex in all compounds studied (results not shown), showing that these two residues have to be kept unchanged in the newly designed caspase-2 inhibitors.

II-2.2/Amino Group Protection of the First Residue

Figure 5:
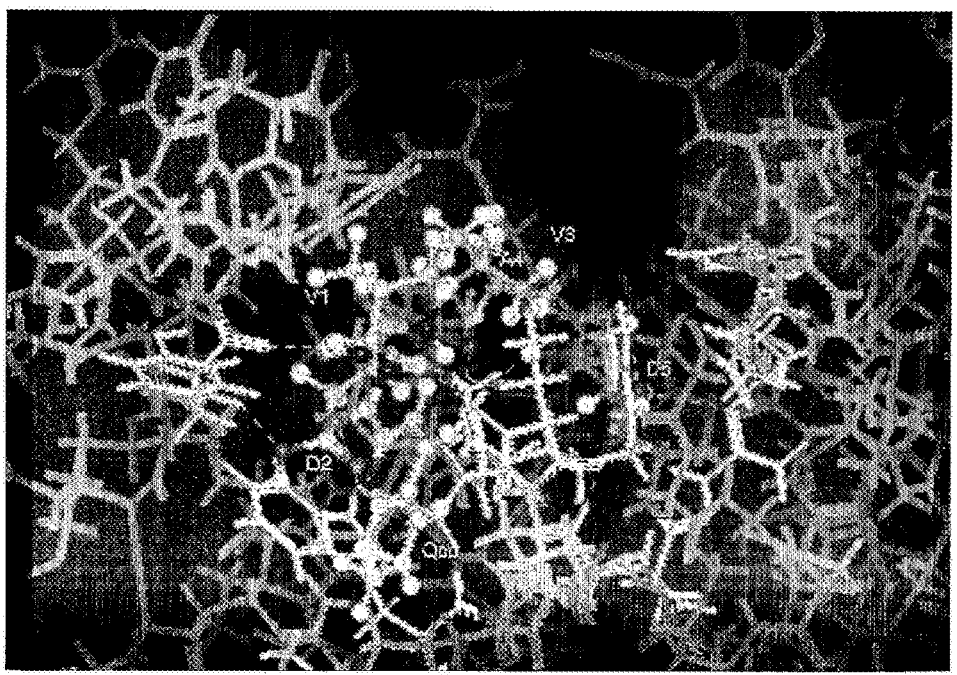
FIG. 5: the superposition of Ac-LDESD(SEQ ID NO:14)-cho 1 and Qco-VDVAD(SEQ ID NO:9)-cho 13 in the active site of caspase-2.

In order to identify more potent inhibitors of the caspase-2 enzyme, the effect of different protecting groups for the amino function of the first residue on the stability of the inhibitor-enzyme complex was studied. For this purpose, used four different pentapeptide sequences were used: LDESD(SEQ ID NO:14), VDVAD(SEQ ID NO:9), LDEAD (SEQ ID NO:7) and VDEAD(SEQ ID NO:1). The results are shown below (the abbreviations used are defined at the end of the document): (a) LDESD(SEQ ID NO:14) series. The complex formed between the caspase-2 enzyme and compounds± (Ac-LDESD(SEQ ID NO:14)-cho, $E_{min}$=−76.6 Kcal/mol), 2 (Qop-LDESD(SEQ ID NO:14)-cho, $E_{min}$=−8.3 Kcal/mol), 4 (Suc-LDESD(SEQ ID NO:14)-cho, $E_{min}$=−85.7 Kcal/mol), 5 (Mal-LDESD(SEQ ID NO:14)-cho, $E_{min}$=−128.6 Kcal/mol), 6 (Qmal-LDESD(SEQ ID NO:14)-cho, $E_{min}$=−53.8 kcal/mole), or 31. (Oxa-LDESD(SEQ ID NO:14)-cho, $E_{min}$=−9.5 Kcal/mol) indicate that (i) the succinyl (Suc) and the malonyl (Mal) groups allow much better inhibition of the caspase-2 enzyme than acetyl group
(ii) the 3-oxo-3-quinolinylpropionyl (Qop), 3-(2-quinolinyl)malonyl (Qmal), and oxalyl (Oxa) lead to the formation of less stable enzyme-inhibitor complexes than the acetyl group.
  (b) VDVAD(SEQ ID NO:9) series. The complexes formed between caspase-2 and compounds 8 (Ac-VDVAD(SEQ ID NO:9)-cho, $E_{min}$=−85.4 Kcal/mol), 9 (Qop-VDVAD(SEQ ID NO:9)-cho, $E_{min}$=−14.2 Kcal/mol), 10 (Mal-VDVAD(SEQ ID NO:9)-cho, $E_{min}$=−134.9 Kcal/mol), 11 (Suc-VDVAD(SEQ ID NO:9)-cho, $E_{min}$=−91.9 Kcal/mol), 12 (Qmal-VDVAD(SEQ ID NO:9)-cho, $E_{min}$=−59.0 Kcal/mol), 13 (Qco-VDVAD(SEQ ID NO:9)-cho, $E_{min}$=+38.0 Kcal/mol FIG. 5), 17 (Bz-VDVAD(SEQ ID NO:9)-cho, $E_{min}$=−4.8 Kcal/mol), 18 (Z-VDVAD(SEQ ID NO:9)-cho, $E_{min}$=−31.8 Kcal/mol), 19 (Hxa-VDVAD (SEQ ID NO:9)-cho, $E_{min}$=−59.0 Kcal/mol) et 24 (VDVAD(SEQ ID NO:9)-cho, $E_{min}$=−32.0 kcal/mol) indicate that:
(i) the succinyl (Suc) and the malonyl (Mal) groups lead to the formation of more stable enzyme-inhibitor complexes and, thus, better inhibition of the caspase-2 than the acetyl group
(ii) the 3-oxo-3-quinolinylpropionyl (Qop), 2-quinolinylmalonyl (Qmal), 2-quinolinylcarbonyl (Qco), benzoyl (Bz), and hexanoyl (Hxa) groups lead to less potent inhibitors than the acetyl group. As shown with the unprotected pentapeptide 24, the absence of protection on the first residue also leads to the formation of less stable enzyme-inhibitor complexes. It should be noted that the docking was realized with atoms of the enzyme fixed. This could explained the positive values observed for the minimal energy of the 2-quinolinylcarbonyl compounds 13, 23 and 30.

TABLE 1

Minimal energy (Kcal/mol) of some inhibitor - caspase-2 complexes.

| Inhibitor | $E_{van\ der\ Waals}$ | $E_{coulombic}$ | $E_{min}$ |
|---|---|---|---|
| Ac-LDESD-cho 1 | 33.7 | −105.3 | −71.6 |
| Ac-VDVAD-cho 8 | −6.7 | −78.7 | −85.4 |
| Qco-VDVAD-cho 13 | 54.2 | −16.2 | +38.0 |

Ac-LDESD(SEQ ID NO:14)-cho, Ac-VDVAD(SEQ ID NO:9)-cho and Qco-VDVAD(SEQ ID NO:9)-cho are described. This series also indicates that Qco-VDVAD(SEQ ID NO:9)-cho 13 appears to be a less potent inhibitor of the caspase-2 enzyme. Indeed, as shown in Table 1 above, when compound 8 was replaced by compound 13 both electric ($E_{coulombic}$) and hydrophobic ($E_{van\ der\ waals}$) components of $E_{min}$ was increased. Tables 2 and 3 below show the contribution of the different residues (V1, D2, V3, A4 and D5) and that of the protecting group (acetyl and 2-quinolinylcarbonyl) on the stabilization of the inhibitor-caspase-2 complex. These results indicate that the substitution of the acetyl group by the 2-quinolinylcarbonyl group (Table 2) lead to weaker interactions between the valine in position 1 (V1) and the caspase-2 active site
weaker interactions between the carbonyl (C=O) function the protecting group and the enzyme
an unstable enzyme-inhibitor complex by the sterically hindered 2-quinolinylcarbonyl group.

TABLE 2

Contribution of the different residues and of the acetyl group on the stabilization of Ac-VDVAD(SEQ ID NO: 9)-cho 8 - caspase-2 complex (Kcal/mol).

| Substituent | $E_{van\ der\ Waals}$ | $E_{coulombic}$ | $E_{min}$ |
|---|---|---|---|
| Acetyl (C=O) | −2.0 | −32.9 | −34.9 |
| V1 | 0.7 | −0.5 | 0.2 |
| D2 | −3.8 | −36.2 | −40.0 |
| V3 | 0.7 | 12.7 | 13.4 |
| A4 | −1.5 | 9.0 | 7.5 |
| D5 | −0.8 | −30.9 | 31.7 |

TABLE 3

Contribution of the different residues and of the 2-quinolinylcarbonyl group on the stability of Qco-VDVAD(SEQ ID NO: 9)-cho 13 - caspase-2 complex (Kcal/mol).

| Substituent | $E_{van\ der\ Waals}$ | $E_{coulombic}$ | $E_{min}$ |
|---|---|---|---|
| 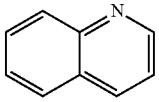 | 57.7 | 19.1 | 76.9 |
| C=O of Qco | 0.4 | −7.4 | −6.9 |
| V1 | 2.0 | 16.7 | 18.7 |
| D2 | −4.3 | −35.8 | −40.1 |
| V3 | 0.5 | 12.9 | 13.4 |
| A4 | −1.5 | 9.1 | 7.6 |
| D5 | −0.7 | −30.9 | −31.6 |

The Qco-VDVAD(SEQ ID NO:9)-CH$_2$O(2,6-difluorophenyl) synthesized in the laboratory was shown to be a potent inhibitor of caspase-2 (IC$_{50}$=80 nM). This indicates that there might be a modulation of the enzyme during the formation of the enzyme-inhibitor complex so as to induce a better fit of the inhibitor into the caspase-2 active site. Another explanation could be the binding of this type of compound into an allosteric site an the enzyme (see also compounds (13, 23 and 32, FIG. 1).

Further studies with unfixed caspase-2 residues will be undertaken in order to gain insight into observed biological results of the Qco-VDVAD(SEQ ID NO:9)-CH$_2$O(2,6-difluorophenyl).

(c) LDEAD(SEQ ID NO:7) series. The study of compounds 14 (Ac-LDEAD(SEQ ID NO:7)-cho, $E_{min}$=−1337 kcal/mole), 15 (Mal-LDEAD(SEQ ID NO:7)-cho, $E_{min}$=−179.2 Kcal/mol), 16 (Memal-LDEAD(SEQ ID NO:7)-cho, $E_{min}$=−145.9 Kcal/mol), 28 (Mac-LDEAD(SEQ ID NO:7)-cho, $E_{min}$=−97.6 Kcal/mol) and 29 (Ps-LDEAD(SEQ ID NO:7)-cho, Emin=−71.6 Kcal/mol) provide further confirmation of the better stabilization of the enzyme-inhibitor complex by the malonyl (Mal) and the 3-methylmalonyl (Memal) groups than the acetyl group. This series also shows that the 3-methoxyacetyl (Mac) and the phenylsulfonyl (Ps) groups lead to less potent inhibitors than the acetyl group.

(d) VDEAD(SEQ ID NO:1) series. The results obtained with compounds 20 ((Ac-VDEAD(SEQ ID NO:1)-cho, Emi$_\pi$=−113.2 kcal/mole) and 21 (Memal-VDEAD(SEQ ID NO:1)-cho, $E_{min}$=−126.1 Kcal/mol) further demonstrate that that 3-methylmalonyl (Memal) leads to more potent inhibitors than the acetyl group.

II-2.3/Configuration of the D5 Residue

Figure 6:
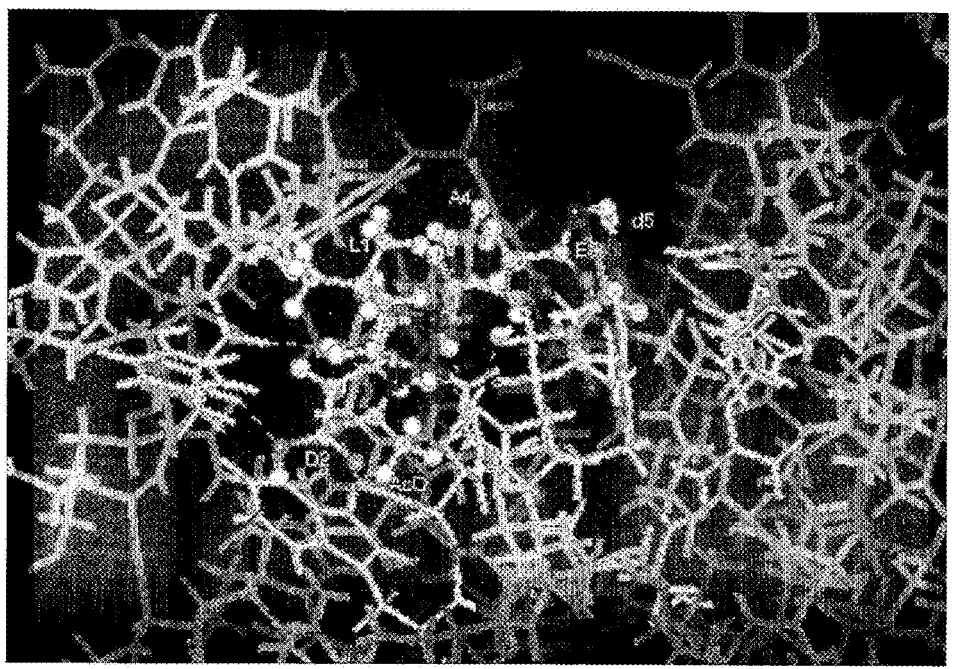
FIG. 6: the superposition of Ac-LDESD(SEQ ID NO:14)-cho 1 and Ac-LDEAD(SEQ ID NO:7)-cho 25 in caspase-2 active site.

To study the effect on the configuration of the D5 residue of the inhibition of caspase-2, compound 30 (d5, $E_{min}$=+65.5 Kcal/mole) was also studied. Comparison the minimal energy ($E_{min}$) so observed to that of compound 13, ($E_{min}$=+38.0 Kcal/mol) and compound 30 (d5, Emin=+65.5 Kcal/mol) clearly shows that D-configuration at position 5 leads to diminished potency of the inhibitor. This was confirmed by comparing the energy of the complex formed between the enzyme and compound 20 (Ac-LDEAD(SEQ ID NO:7)-cho, $E_m$in=−133.7 kcal/mole) and compound 25 (Ac-LDEAD (SEQ ID NO:7)-cho, $E_{min}$=−107.8 Kcal/mol). Indeed, as shown in FIG. 6, the complex formed between compound 25 and the enzyme would be deprived of the C—S covalent bond between D5 carbonyl and the thiol group of the caspase-2 cysteine A155 residue. Moreover, the hydrogen bonds between the side chain of this aspartic acid residue and the enzyme would be lost.

II-2.4/Truncated Peptides

The results obtained with compounds 22 (Z-VAD-cho, $E_{min}$=−7.6 Kcal/mol) and 23 (Z-VD-cho, $E_{min}$=+66.6 Kcal/mol) indicate that these truncated peptides are less potent inhibitors of caspase-2.

II-3/Conclusions

II-3.1/Peptide Sequence

Figure 7:
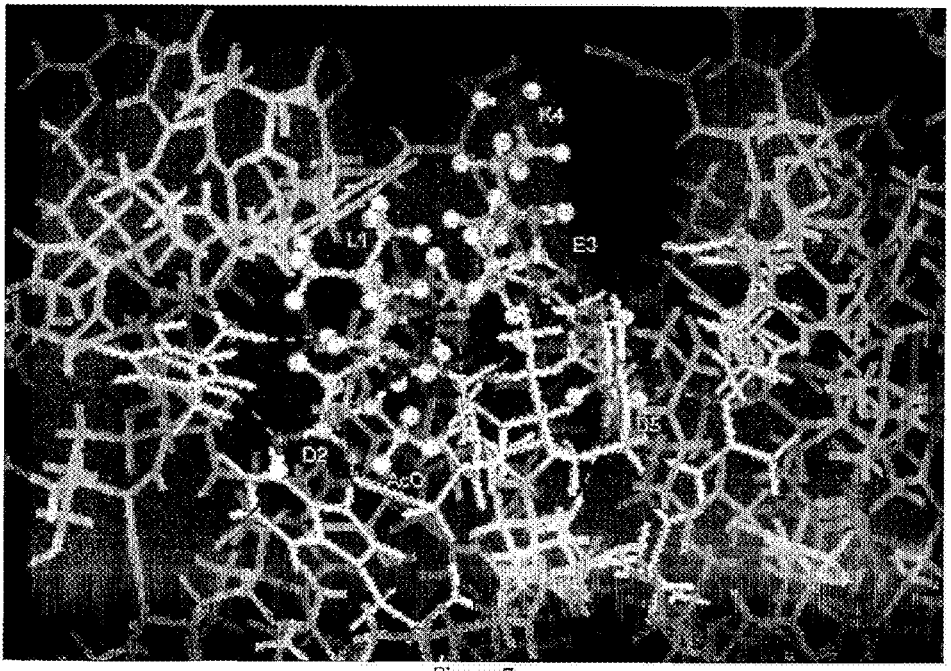
FIG. 7: the superposition of Ac-LDESD(SEQ ID NO:14)-cho 1 and Ac-LDEKD(SEQ ID NO:5)-cho 27 in the active site of caspase-2.

This search for new caspase-2 inhibitors shows that the
(a) VDVAD(SEQ ID NO:9) sequence leads to slightly more potent inhibitors of caspase-2 than the LDESD (SEQ ID NO:14) sequence (compared to compounds 1 and 8, 2 and 9, 4 and 11, 5 and 10, 6 and 12)
(b) LDEAD(SEQ ID NO:7), LDEGD(SEQ ID NO:2) and LDEKD(SEQ ID NO:5) sequences leads to more potent caspase-2 inhibitors than the VDVAD(SEQ ID NO:9) sequence (compared to compounds 8 to 14, 10 to 15, 8 to 26, and 8 to M.
(c) VDESD(SEQ ID NO:4) (see compound 7) and VDEAD (SEQ ID NO:1) (see compound 20) sequences provide better inhibitors of the caspase-2 enzyme than the VDVAD(SEQ ID NO:9) sequence II-3.2/Routing and Radioactive Labeling This study clearly shows that caspase-2 active site can accommodate different residues at position 4 of the pentapeptidic inhibitors. In compound 27, for example, this is achieved by the positioning of the side chain of the lysine residue (K4) outside the enzyme's active site as shown in FIG. 7.

The highly stable complex formed in this case (compound 27, substitution serine by lysine at position 4) indicate that fluorescent chromophores (for example fluoresceine isothiocyanate (FITC), rhodamine, and Alexa Fluor) or biotin could be introduced at this position, thereby allowing routing of these pentapeptidic inhibitors in the biological system.

This ability of the caspase-2 enzyme to accommodate several residues at position 4 also indicate that one could introduce a halogenated phenylalanine or tyrosine residue at this position for the purpose of radioactive labeling.

II-3.3/Configuration of the Aspartic Acid at Position 5

The usual procedures for the synthesis of aldehyde or methylketone analogues of compound 1 (FIG. 1) sometimes give rise to epimerization of the D5 residue. The mixture of isomers formed are sometimes difficult to isolate. As indicated in section II-2.3/the so-formed D-epimer is less potent than the L-isomer due to loss of both hydrogen and covalent interactions between this residue and the enzyme.

II-3.4/Protection of the Amino Function at Position 1

Substitution of the acetyl group by other protective groups has led to the following conclusions and remarks:
(a) the 2-quinolinylcarbonyl (Qco) group appears to lead an unstable enzyme-inhibitor-complex (see compounds 13, 23 and 30). This observation was not strictly in accordance to the biological data obtained with Qco-VD (Ome)VAD(Ome)-CH$_2$O(2,6-difluorophenyl) showing that an induced fit mechanism might be operating during the formation of the inhibitor-caspase-2 complex. Allosteric binding could also explain this observed difference between the in silico and the in vitro results. VDVAD is SEQ ID NO: 9.

(b) among the protecting groups studied, the malonyl (Mal) appears to lead to much better inhibition of caspase-2 than the other groups (see compound 15, $E_{min}=-179.2$ Kcal/mol). Furthermore, the 3-methylmalonyl group (Memal, compound 16, $E_{min}=-145.9$ Kcal/mol) also appears to lead to highly stabilized enzyme-pentapeptide complexes. If compounds such as 16 could be hydrolyzed by esterases to corresponding derivative 15 before binding to the caspase-2 active site, even more potent inhibition would be observed. Thus, much attention will be focused on this Memal group for designing of novel caspase-2 inhibitors.

II-3.5/Choice of the Leaving Groups

In order to study the effect of the leaving groups on the potency of these inhibitors, pentapeptides bearing different nucleofuges on the D5 residue have been synthesized and evaluated in various biological systems. These leaving groups have been chosen according to their physicochemical properties and their reported biological properties such as toxicities and cellular permeability and retention.

These selected inhibitors thus have the general formula 32:

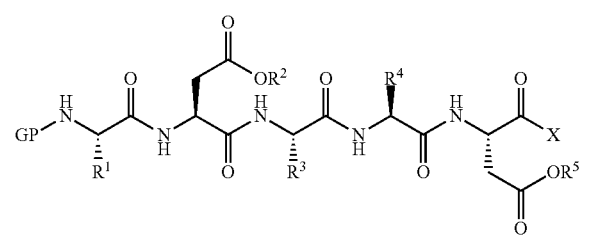

Wherein (i) GP is as above defined with respect to M, and particularly=protecting group such as malonyl, methylmalonyl, 2-quinolinylcarbonyl, succinyl, methylsuccinyl, acetyl, 2-quinolinylmalonyl, heterocyclic ring such as substituted or unsubstituted tetrahydroquinoline, tetrahydroisoquinoline, dihydroacridine, benzazepine, pyrrolidine, morpholine, thiomortholine, piperazine, piperidine, dihydropyridine, benzimidazole, imidazole, imidazoline, pyrrole, pyrrolidine, pyrroline, pyrazole, pyrazoline, pyrazolidine, triazole, piperidine, morpholine, thiomorpholine, piperazine, carbazole, phenothiazine, phenoxazine, dihydrophenazine, dihydrocinnoline, dihydroquinoxaline, dihydronaphthyridine, tetrahydronaphthyridine, dihydroacridine, indole, isoindole, dihydroindole, indoline, indazole, purine, 9,10-dihydrophenanthridine, 5H-dibenzo[b,f]azepine, 10,11-dihydro-5H-dibenzo[b,f]azepine, 3-carboline, pyrido[4,3-b]indole, 2,3,9-triazofluorene, 9-thia-2,10-diazaanthracene, thieno[3,2b]pyrrole, dihydrophenanthrine, Benzyloxycarbonyl, etc. . . . , a hydrogen atom, $C_{1-20}$ aliphatic group, aryl, substituted aryl (ex: 4-nitrophenyl or coumarine derivatives), hetetoaryl (ex. 2-pyridine), substituted heteroaryl, cycloalkyl, naphthyl, substituted naphthyl, $(CH_2)_n$cycloalkyl, $(CH_2)_n$phenyl, $(CH_2)_n$substituted phenyl (ex: 2,6-dihalophenyl), $(CH_2)_n$(1- or 2-naphthyl), $(CH_2)_n$heteroaryl or (un)substituted (2-, 3-, 4-, 5-, 6-, 7- or 8-) quinolinyl, fluorenmethyl GP may also be R, U, $CO(CH_2)_nNH(U)$, $CO(CH_2)_nS(U)$ in which:

U is (un)substituted (2-, 3-, 4-, 5-, 6-, 7- or 8-) quinolinyl, $C_{1-20}$ straight chain or branched alkyl, $(CH_2)_n$cycloalkyl, $(CH_2)_n$phenyl, $(CH_2)_n$substituted phenyl, $(CH_2)_n$(1- or 2-naphthyl), $(CH_2)_n$heteroaryl, biotin, dinitrophenyl (DNP), iodoacetamides, DTNB, COR (ex. 2-quinolinylcarbonyl), COOR, $CO(CH_2)_nNH(Z)$, Acridine derivatives (Red, yellow, orange . . . ), Fluorescein derivatives (fluorescein, FITC, FAM (carboxyfluorescein), 5-(and-6)-carboxynaphthofluorescein, carboxyfluorescein, BCECF, naptofluorescein . . . ), Oregon Green® (2',7'-difluorofluorescein) dyes (Oregon Green® 488, Oregon Greene 514 . . . ), BODIPY® (4,4-difluoro-5,7-dimethyl-4-bora-3a,4a-diaza-s-indacene-3-propionic acid) dyes (BODIPY FL, BODIPY TMR, BODIPY TR, BODIPY 630/650, BODIPY 630/665), Bimane, Coumarin derivatives (aminomethylcoumarin (AMC), AMCA, aminocoumarin, diethylaminocoumarin hydroxymethylcoumarin; hydroxycoumarin, methoxycoumarin, AFC, . . . ), Cyanin derivatives (phycocyanin, allophycocyanin (APC), CY3.18, CY5.18, Cy2, Cy3, Cy3.5, Cy5, Cy5.5, Cy7 . . . ), Erythrin/Phycoerythrin derivatives (R-Phycoerythrin (PE), B-Phycoerythrin . . . ), APC/PE-Cy conjugates (PE-Cy5 conjugates, PE-Cy7 conjugates, APC-Cy7 conjugates . . . ), Calcein derivatives (calcein, SNAFL calcein . . . ), DANS, DANSA, Cascade Blue, Lucifer yellow, NBD, Red 613, Fluor X, Rhodamine derivatives(Rhodamine 123, Rhodamine 110, Rhodamine B, Rhodamine 6A, Rhodamine 6G, TRITC, X-Rhodamine, sulphorhodamin, Rhodamine Red-X, Lissamine™ rhodamine B, DHR, Rhodamine Green . . . ), PerCP, Texas Red, TruRed, Alexa Fluo® (Alexa Fluor 350, Alexa Fluor 430, Alexa Fluor 488, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, Alexa Fluor 750 . . . ), Q-DOTs™ derivatives (655,605, 585,525, . . . ), SNARF, Zenon™ derivatives (Zenon™ Alexa Fluor® 350, Zenon™ Alexa Fluor® 488, Zenon™ Alexa Fluor® 555, Zenon™ Alexa Fluor® 594, Zenon™ Alexa Fluor® 647, Zenon™ Allophycocyanin, Zenon™ Biotin-XX, Zenon™ R-Phycoerythrin . . . ); NBD, Texas Red®, QSY® dyes (QSY® 7, QSY® 9, QSY® 35, QSY® 21), Hoechst (33342, 33258), DAPI, Chromomycin A3, Mithramycin, SYTOX (Blue, Green, Orange), Ethdium, Ethidium Bromide, 7-AAD, TOTO dyes, YOYO dyes, TO-PRO dyes, BOBO dyes, JO-PRO dyes, LO-PRO dyes, PO-PRO dyes, YO-PRO dyes, Thiazole Orange, Propidium Iodide (PI), LDS 751, Indo® dyes (Indo-1 . . . ), Fluo® dyes (Fluo-3 . . . ), DCFH, pNA, SYBR green II, SyPro (Orange, Ruby), EDANS, IR800, DiI, DiO, DiD, SNARF® derivatives, Fura dyes, QUIN dyes, NANOGOLD particules, NANOGOLD maleimide, AlexaFluor FluoroNANOGOLD, AlexaFluor FluoroNANOGOLD streptavidin, malachite green, Dabcyl, Dabsyl, Cascade yellow, dansyl, Dapoxyl, PyMPO, Pyrene, benzoxadiazole derivatives, strepavidin-/neutravidin-)biotin-labeled fluorescent microspheres, CMNB-caged fluorescein conjugate of streptavidin, calcofluor white, nile red, Y66F, Y66H, EBFP, GFP wild type, QFP mutants H9/P4/P9/P11/W, GFPuv, ECFP, Y66W, S65A, S65C, S65L, S65T, EGFP, EYFP, ECFP, DsRed1, DsRed2, NANOGOLD® particles, streptavidin-Nanogold®, Monomaleido Nanogold®, Mono-Sulfo-NHS-Nanogold®, Monoamino Nanogold®, positively/negatively charged Nanogold® (NN, NHSN, NHSNA, NHSNS), Non-Functionalized Nanogold®, Monomaleido Nanogold®, Mono-Sulfo-NHS-Nanogold®, Monoamino Nanogold®, Non-functional Nanogold®, Nanogold®-conjugates, Nanogold®-Streptavidin, lipide-Nanogold (Palmitoyl Nanogold®, DPPE Nanogold®, Palmitoyl Undecagold, DPPE Undecagold), Ni-NTA-Nanogold®, Alexa Fluor® 488 FluoroNanogold, Alexa Fluor® 594 FluoroNanogold, Fluorescein FluoroNanogold, HRP substrate-Nanogold, colorimetric group (pNA . . . ) or bioluminescent substrates, radioisotopes a radioisotope (ex: $I^{125}$, $H^3$, $S^{35}$, $C^{14}$, $P^{33}$, $P^{32}$, $Cr^{51}$, $Ca^{45}$, $Fe^{59}$, $Ni^{63}$, $Ba^{133}$, $Cs^{137}$, $Eu^{152}$, $Ra^{226}$, $Xe^{133}$, technétium 99, thallium 201). In a non restrictive embodiment, a fluorogenic moiety which emits light, transferts electrons to acceptor (FRET) or is quenched after cleavage, or suuceptible to FLIP, FLIM, FRAP technologies.

(ii) X=hydrogen atom, OR, NHR, SR, $CH_2OR$, $CH_2NHR$, $CH_2SR$, $CH_2OR$ and $CH_2Y$, in which R=acyl, alkyl, substituted alkyl, aryl, substituted aryl and in is an aliphatic group, an aryl group, an aralkyl group, a carbocyclic group, an alkyl carbocyclic group, or a heterocyclic group which Y=halogen atom (F, Cl, Br or I) or $N_2$.

X may also be $C_{1-20}$ aliphatic, substituted or unsubstituted aryl, cycloalkyl, naphthyl, substituted naphthyl, 2-benzoxazolyl, substituted 2-oxazolyl, $(CH_2)_n$cycloalkyl, $(CH_2)_n$phenyl, $(CH_2)_n$substituted phenyl, $(CH_2)_n$(1- or 2-naphthyl), $(CH_2)_n$heteroaryl, $CH_2N^2$, $CH_2Y$, OH, OR, $NH_2$, NHR, $NR_2$, SR, COR, $CO_2R$, $CONR_2$, $CH_2OCOR$, $CH_2O$—CO aryl, $CH_2O$—C(O) substituted aryl (ex: 2,6-dimethylbenzoyloxymethyl), $CH_2O$—C(O) substituted aryl, $CH_2O$—C(O) heteroaryl, $CH_2O$—C(O) substituted heteroaryl or $CH_2OPOR_2$;

in which R=hydrogen atom, $C_{1-20}$ aliphatic group, aryl, substituted aryl (ex: 4-nitrophenyl or coumarine derivatives), hetetoaryl (ex. 2-pyridine), substituted heteroaryl, cycloalkyl, naphthyl, substituted naphthyl, $(CH_2)_n$cycloalkyl, $(CH_2)_n$phenyl, $(CH_2)_n$substituted phenyl (ex: 2,6-dihalophenyl), $(CH_2)_n$(1- or 2-naphthyl), $(CH_2)_n$heteroaryl or (un)substituted (2-, 3-, 4-, 5-, 6-, 7- or 8-) quinolinyl, fluorenmethyl.

in which, Y is an electronegative leaving group including halogens such as F, Cl, Br or I, aryl or alkylsulfonyloxy groups, trifluoromethanesulfonyloxy, OR, SR, COOR, $OP(O)R_2$ wherein R is an aliphatic group, an aryl group, an aralkyl group, a carbocyclic group, an alkyl carbocyclic group, or a heterocyclic group;

in which X=U is (un)substituted (2-, 3-, 4-, 5-, 6-, 7- or 8-) quinolinyl, $C_{1-20}$ straight chain or branched alkyl, $(CH_2)_n$cycloalkyl, $(CH_2)_n$phenyl, $(CH_2)_n$substituted phenyl, $(CH_2)_n$(1- or 2-naphthyl), $(CH_2)_n$heteroaryl, biotin, dinitrophenyl (DNP), DTNB, Acridine derivatives (Red, yellow, orange . . . ), Fluorescein derivatives (fluorescein, FITC, FAM (carboxyfluorescein), 5-(and-6)-carboxynaphthofluorescein, carboxyfluorescein, BCECF, naptofluorescein . . . ), Oregon Green® (2',7'-difluorofluorescein) dyes (Oregon Green® 488, Oregon Green® 514 . . . ), BODIPY® (4,4-difluoro-5,7-dimethyl-4-bora-3a,4a-diaza-s-indacene-3-propionic acid) dyes (BODIPY FL, BODIPY TMR, BODIPY TR, BODIPY 630/650, BODIPY 630/665 . . . ), Bimane, Coumarin derivatives (aminomethylcoumarin (AMC), AMCA, aminocoumarin, diethylaminocoumarin hydroxymethylcoumarin; hydroxycoumarin, methoxycoumarin, AFC, . . . ), Cyanin derivatives (phycocyanin, allophycocyanin (APC), CY3.18, CY5.18, Cy2, Cy3, Cy3.5, Cy5, Cy5.5, Cy7 . . . ), Erythrin/Phycoerythrin derivatives (R-Phycoerythrin (PE), B-Phycoerythrin . . . ), APC/PE-Cy conjugates (PE-Cy5 conjugates, PE-Cy7 conjugates, APC-Cy7 conjugates . . . ), Calcein derivatives (calcein, SNAFL calcein . . . ), DANS, DANSA, Cascade Blue, Lucifer yellow, NBD, Red 613, Fluor X, Rhodamine derivatives (Rhodamine 123, Rhodamine 110, Rhodamine B, Rhodamine 6A, Rhodamine 6G, TRITC, X-Rhodamine, sulphorhodamin, Rhodamine Red-X, Lissamine™ rhodamine B, DHR, Rhodamine Green . . . ), PerCP, Texas Red, TruRed, Alexa Fluo® (Alexa Fluor 350, Alexa Fluor 430, Alexa Fluor 488, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, Alexa Fluor 750 . . . ), Q-DOTs™ derivatives (655,605, 585,525, . . . ), SNARF, Zenon™ derivatives (Zenon™ Alexa Fluor® 350, Zenon™ Alexa Fluor® 488, Zenon™ Alexa Fluor® 555, Zenon™ Alexa Fluor® 594, Zenon™ Alexa Fluor® 647, Zenon™ Allophycocyanin, Zenon™ Biotin-XX, Zenon™ R-Phycoerythrin); NBD, Texas Red®, QSY® dyes (QSY® 7, QSY® 9, QSY® 35, QSY® 21), Hoechst (33342, 33258), DAPI, Chromomycin A3, Mithramycin, SYTOX (Blue, Green, Orange), Ethdium, Ethidium Bromide, 7-AAD, TOTO dyes, YOYO dyes, TO-PRO dyes, BOBO dyes, JO-PRO dyes, LO-PRO dyes, PO-PRO dyes, YO-PRO dyes, Thiazole Orange, Propidium Iodide (PI), LDS 751, Indo® dyes (Indo-1 . . . ), Fluo® dyes (Fluo-3 . . . ), DCFH, pNA, SYBR green II, SyPro (Orange, Ruby), EDANS, IR800, DiI, DiO, DiD, SNARF® derivatives, Fura dyes, QUIN dyes, NANOGOLD particles, NANOGOLD maleimide, AlexaFluor FluoroNANOGOLD, AlexaFluor FluoroNANOGOLD streptavidin, malachite green, Dabcyl, Dabsyl, Cascade yellow, dansyl, Dapoxyl, PyMPO, Pyrene, benzoxadiazole derivatives calorimetric group (pNA . . . ) or bioluminescent substrates, a radioisotope (ex: $I^{125}$, $H^3$, $S^{35}$, $C^{14}$, $P^{33}$, $P^{32}$, $Cr^{51}$, $Ca^{45}$, $Fe^{59}$, $Ni^{63}$, $Ba^{133}$, $Cs^{137}$, $Eu^{152}$, $Ra^{226}$, $Xe^{133}$, technétium 99, thallium 201). In a non restrictive embodiment, a fluorogenic moiety which emits light, transfers electrons to acceptor (FRET) or is quenched after cleavage, or susceptible to FLIP, FLIM, FRAP technologies.

(iii) $R^1$, $R^3$ and $R^4$=natural and non natural amino acid side chains, the absolute configuration of each amino acid is either L or D (iv) $R^2$ and $R^5$=hydrogen atom, alkyl, substituted alkyl, aryl and substituted aryl (x) n is 0 to 20

As used herein, the following definitions shall apply unless otherwise indicated. The abbreviations Qco stand for quinolinylcarbonyl. The term "aliphatic" herein means straight chained or branched C1_20 hydrocarbons which are completely saturated or which contain one or more units of unsaturation. The term "alkyl" used alone or as part of a larger moiety refers to both straight or branched chains containing one to twenty carbon atoms. The term "aryl" refers to mono cyclic or polycyclic aromatic ring groups having five to fourteen atoms, such as phenyl, naphthyl or anthryl. The term "heterocyclic group" refers to saturated or unsaturated polycyclic or monocyclic ring systems containing one or more heteroatoms and a ring size of three to nine such as furanyl, thienyl, pyrrolyl, pyrrolinyl, pyrrolidinyl, dioxolanyl, oxazolyl, thiazolyl, imidazolyl, imidazolidinyl, imidazolidinyl, pyrazolyl, pyrazolinyl, pyrazolidinyl, isoxalolyl, isothiazolyl, oxadiazolyl, dioxanyl, morpholinyl, dithianyl, thiomorpholinyl, pyridazinyl, pyrimidinyl, pyrazinyl, piperazinyl, triazinyl, trithianyl, indolizinyl, indolyl, isoindolyl, indolinyl, benzofuranyl, benzothiophenyl, indazolyl, benzamidazolyl, benzthiazolyl, purinyl, quinolizinyl, quinolinyl, isoquinolinyl, cinnolinyl, phthalazinyl, quinazolinyl, quinoxalinyl, 1,8-naphthyridinyl, pteridinyl, quinuclidinyl, carbazolyl, acridinyl, phenazinyl, phenothiazinyl, or phenoxazinyl. "Heteroaryl" refers to a heterocyclic ring that is aromatic. The term "carbocyclic group" refers to unsaturated monocyclic or polycyclic carbon ring systems of three to fourteen carbons which may be fused to aryl or heterocyclic groups. An aliphatic, alkyl, aryl, heteroaryl (ex: quinoline), heterocyclyl, or carbocyclyl, used alone or as part of a larger moiety, refers to substituted or unsubstituted groups. When substituted, these groups may contain one or more substituents. These substituents can be halogen (F, Cl, Br, I), OH, U, $CO(CH_2)_nNH(U)$, $CO(CH_2)_nS(U)$, OR, SR, $NH_2$, NHR, $NR_2$, OCOR, $OP(O)R_2$ wherein R is an aliphatic group, an aryl or substituted group, an aralkyl group, a carbocyclic group, an alkyl carbocyclic group, a heterocyclic group or a radio-isotope (ex: $I^{125}$, $H^3$, $S^{35}$, $C^{14}$, $P^{33}$, $F^{32}$, $Cr^{51}$, $Ca^{45}$, $Fe^{59}$, $Ni^{63}$, $Ba^{133}$, $Cs^{137}$, $Eu^{152}$, $Ra^{226}$, $Xe^{133}$, technétium 99, thallium 201). FITC stands for fluorescein isothiocyanate.

Although this study was realized with peptide aldehydes, emphasis will be put on the therapeutically reliable compounds like the methylketone derivatives or phenoxy derivatives because the aldehydes are prone to degradation during transport. Moreover, these derivatives appear to be metabolically more stable than the corresponding aldehydes, and lead to irreversible caspase inhibition.

III/Functional Validation of Sequences and Inhibitors of Caspase-2;

III-1/Methodology

Figure 8:
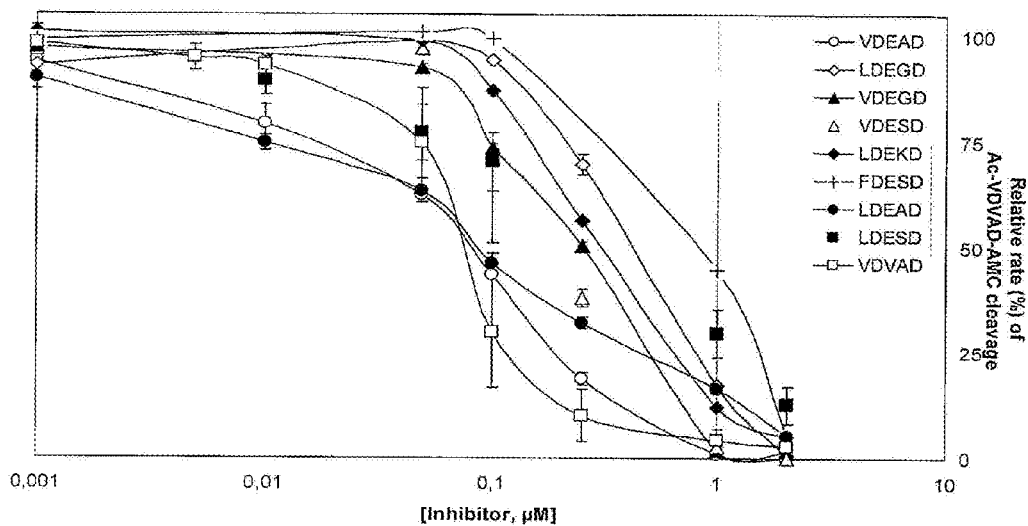
FIG. 8: the inhibition curves of newly designed pentapeptidic inhibitors against human recombinant caspase-2.

Newly designed inhibitors (Ac-LDEAD(SEQ ID NO:7)-CHO, Ac-VDEAD(SEQ ID NO:1)-CHO . . . ) were compared to Ac-VDVAD(SEQ ID NO:9)-CHO in in vitro caspase-2 cleavage assay according to the following protocol (FIG. 8). Human recombinant caspases (25-50 U; QuantiZyme™ Assay System, BIOMOL, Plymouth, Pa., USA) were pre-incubated 30 min with inhibitors (0.005-2 µM) in final 100 µl final assay buffer (50 mM HEPES, pH 7.4, 100 mM NaCl, 0.1% CHAPS, 10 mM DTT, 1 mM EDTA, 10% glycerol) and then mixed with 200 µM of the fluorogenic caspase substrates (BIOMOL) Ac-VDVAD(SEQ ID NO:9)-AMC. An $IC_{50}$ value corresponding to the concentration that could inhibit 50% of caspase activity was determined from the dose-response sigmoid curve. The cleavage of AMC-based substrates by human recombinant caspases 1-10 was measured after 2 h at 37° C. on a fluorescence microplate reader by monitoring emission at 510 nm upon excitation at 405 nm.

III-2/Results and Discussions

Figure 9:
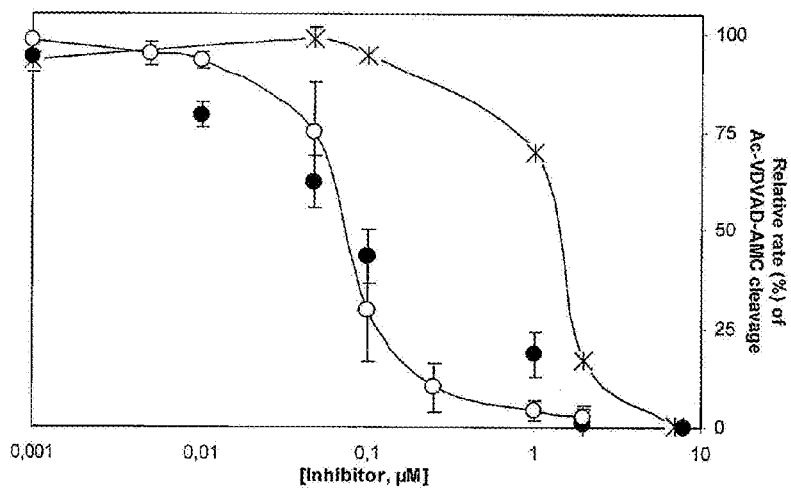
FIG. 9: three typical pattern of human recombinant caspase-2 inhibition by pentapeptidic inhibitors of the invention.
Figure 10:
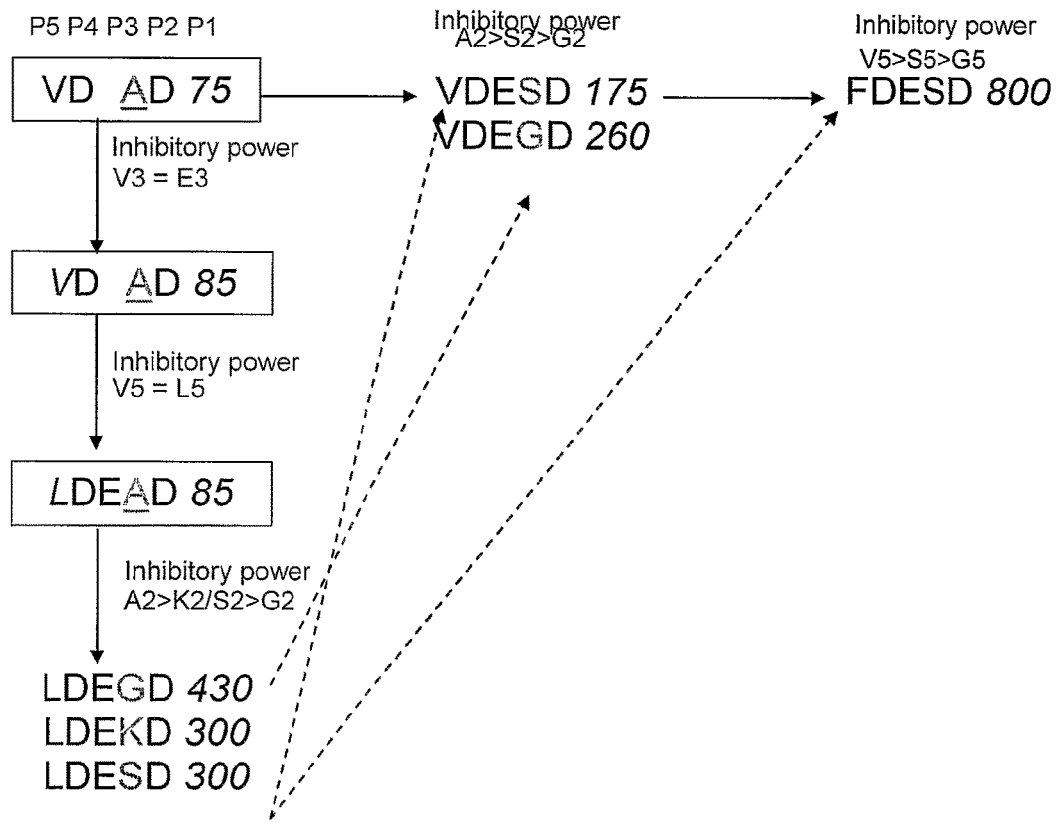
FIG. 10: experimental rational for caspase-2 inhibition (IC50 are in nM)

As determined by molecular docking and in vitro caspase assays, LDEAD(SEQ ID NO:7)- and VDEAD(SEQ ID NO:1)-based compounds were putative efficient caspase-2 inhibitors, with higher $E_{min}$ and lower $IC_{50}$ values against caspase-2 than provided by usual VDVAD(SEQ ID NO:9)- or LDESD(SEQ ID NO:14)-based inhibitors (FIG. 8; Table 1 and 4). Other newly designed pentapeptidic based-caspase-2 inhibitors have higher $IC_{50}$ than LDEAD(SEQ ID NO:7)- and VDEAD(SEQ ID NO:1)-based compounds, but may be considered (according to their $IC_{50}$ value) as moderate (VDESD (SEQ ID NO:4), VDEGD(SEQ ID NO:22), LDEKD(SEQ ID NO:5)) or weak (LDEGD(SEQ ID NO:2), FDESD(SEQ ID NO:6)) caspase-2 inhibitors (FIG. 8 and Table 4). Nevertheless, the inhibitory intrinsic potency of these pentapeptidic-based compounds to inhibit caspase-2 may be also defined according to their respective inhibition curve (Table 4 and FIG. 9): group 2 referred to VDVAD(SEQ ID NO:9)-based inhibitor with characteristic sigmoid dose-response; group 1 referred to inhibitors that were relatively more active than VDVAD(SEQ ID NO:9)-based inhibitors against caspase-2 at lower doses, but with similar $IC_{50}$ values (LDEAD(SEQ ID NO:7) and VDEAD(SEQ ID NO:1)); group 3 referred to pentapetidic-based inhibitors that were less active than VDVAD(SEQ ID NO:9)-based inhibitors against caspase-2 at lower doses and that exhibited higher $IC_{50}$ (LDEGD(SEQ ID NO:2), FDESD(SEQ ID NO:6), LDESD(SEQ ID NO:14), LDEKD(SEQ ID NO:5), VDESD(SEQ ID NO:4), VDEGD (SEQ ID NO:22)). Thus, these experimental data provide a consensus for rational design of caspase-2 inhibitors as shown in FIG. 9 (according to the P5P4P3P2P1 common nomenclature of peptidic caspase inhibitors): (i) requirement for D1 and D4; (ii) requirement for V3 or D3; S2 or G2 were tolerated as P2 residue, but V1 is preferred to L1. In such case, LDEAD(SEQ ID NO:7)- and VDEAD(SEQ ID NO:1)-based compounds appeared as more interesting pentapeptidic based-caspase-2 inhibitors, because having both low 1050 and inhibitory potency at lower doses compared to VDVAD (SEQ ID NO:9)-based inhibitors. Such sequences are templates of great interest to produce other chimeric molecules with modifications as described below in N and C terminus for cellular and in vivo purpose.

TABLE 4

Characterisctics of new pentapeptidic-based caspase-2 inhibitors.

| Sequence | SEQ ID NO: | $IC_{50}$ (nM) | $E_{min}$ (kcal/mole) | Group |
|---|---|---|---|---|
| VDEAD | 1 | 85 ± 5 | −113.2 | 1 |
| LDEGD | 2 | 430 ± 12 | −135 | 3 |
| VDEGD | 3 | 260 ± 5 | / | 3 |
| VDESD | 4 | 175 ± 6 | −101.2 | 3 |
| LDEKD | 5 | 300 ± 5 | −125.2 | 3 |
| FDESD | 6 | 800 ± 4 | / | 3 |
| LDEAD | 7 | 85 ± 6 | −133.7 | 1 |
| LDESD | 14 | 300 ± 20 | −76.6 | 2/3 |
| VDVAD | 9 | 75 ± 13 | −85.4 | 2 |

IV/Functional Validation of Sequences and Inhibitors on Caspase-6

IV-1/Methodology

Newly designed inhibitors (Ac-LDEAD(SEQ ID NO:7)-CHO, Ac-VDEAD(SEQ ID NO:1)-CHO) . . . ) were tested against a large panel of caspase (1 to 10) during in vitro cleavage assay according to the following protocol. Human recombinant caspases (25-50 U; Biomol) were pre-incubated 30 min with inhibitors (0.005-2 µM) in final 100 µl final assay buffer (50 mM HEPES, pH 7.4, 100 mM NaCl, 0.1% CHAPS, 10 mM DTT, 1 mM EDTA, 10% glycerol) and then mixed with 200 µM of their specific fluorogenic caspase substrates (BIOMOL) (Ac-YVAD(SEQ ID NO:23)-AMC (caspase-1), Ac-VDVAD(SEQ ID NO:9)-AMC (caspase-2), Ac-DEVD(SEQ ID NO:24)-AMC (caspase-3/-7), Ac-VEID (SEQ ID NO:25)-AMC (caspase-6), Ac-IETD(SEQ ID NO:26)-AMC (caspase-8l-10)$_1$Ac-LEHD(SEQ ID NO:27)-AMC (caspase-9). The cleavage of AMC-based substrates by human recombinant caspases 1-10 was measured after 2 h at 37° C. on a fluorescence microplate reader by monitoring emission at 510 nm upon excitation at 405 nm.

IV-2/Results and Discussions

Figure 14:
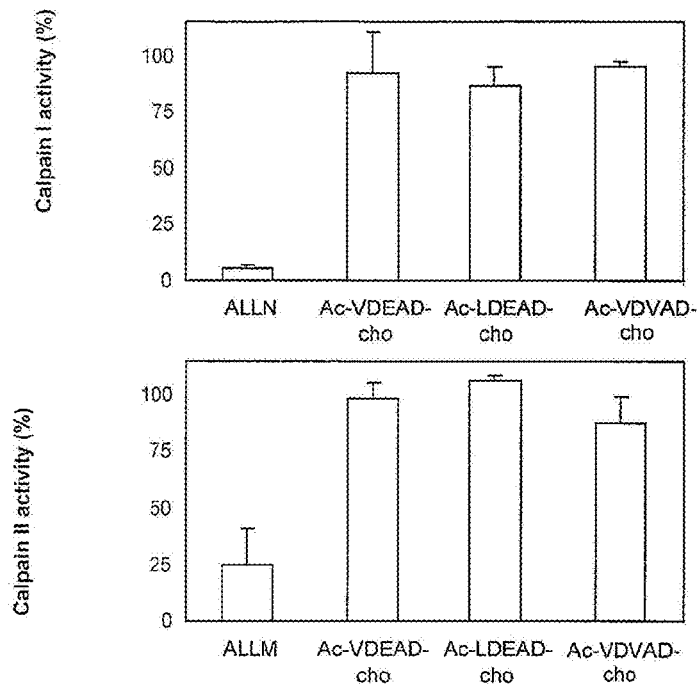
Figure 15:
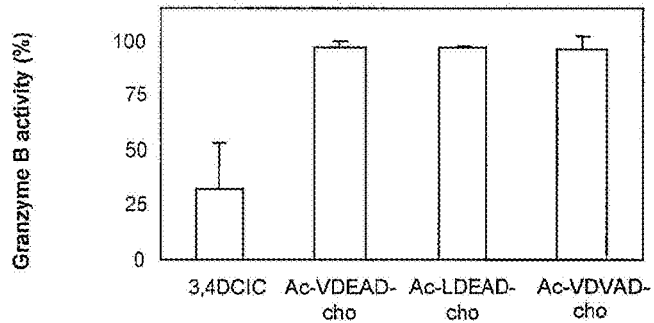
Figure 16:
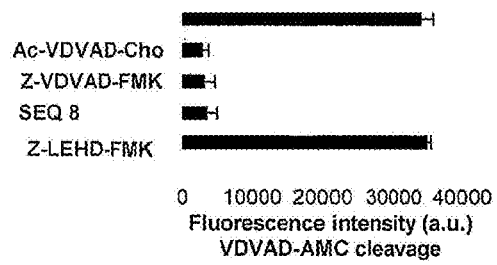

As molecular docking of pentapeptidic sequences with caspase-2 is not predictive for recognition and inhibition of other caspases, inhibition profile of most potent pentapeptidic-based caspase-2 inhibitors (Ac-LDEAD(SEQ ID NO:7)-cho and Ac-VDVEAD(SEQ ID NO:28)-cho) was determined on a panel of human recombinant caspases (FIGS. 14-16).

Figure 11:
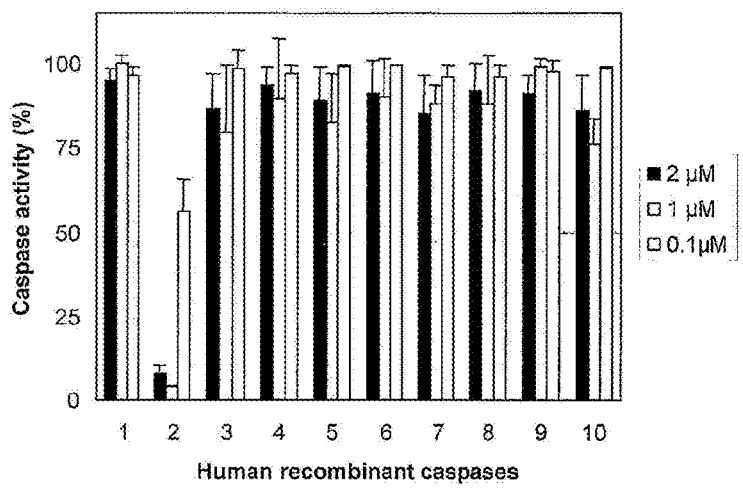
FIG. 11: the inhibition profile of Ac-VDVAD(SEQ ID NO:9)-cho.

Increasing doses of usual Ac-VDVAD(SEQ ID NO:9)-cho caspase-2 inhibitor did not reveal high cross-reaction against other caspases (among an acceptable threshold of less than 20% of inhibition at high doses) (FIG. 11).

Surprisingly, the newly LDEAD(SEQ ID NO:7)- and VDEAD(SEQ ID NO:1)-based inhibitors, show some cross-inhibition against caspase-6 (FIGS. 15 and 16). While these compounds exhibited one hundred nonomolar range to inhibit 50% of caspase-2 activity (Table 4, FIG. 8), they were also able to inhibit caspase-6 with higher IC$_{50}$ (FIGS. 15 and 16) near 2 μM and 0.1-05 μM for LDEAD(SEQ ID NO:7)- and VDEAD(SEQ ID NO:1)-based compounds, respectively. VDEAD(SEQ ID NO:1) is more potent caspase-6 inhibitor than LDEAD(SEQ ID NO:7) (FIGS. 15 and 16). It is the first description of pentapeptidic-based caspase-6 inhibitors.

Figure 12:
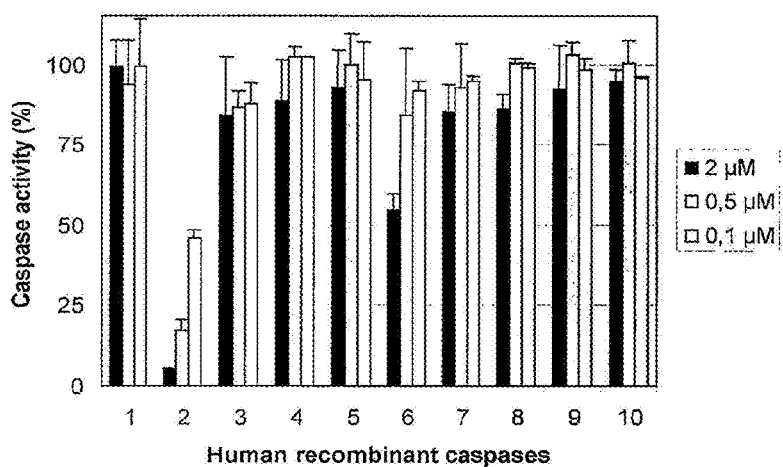
FIG. 12: the inhibition profile of Ac-LD EAD(SEQ ID NO:7)-cho.
Figure 13:
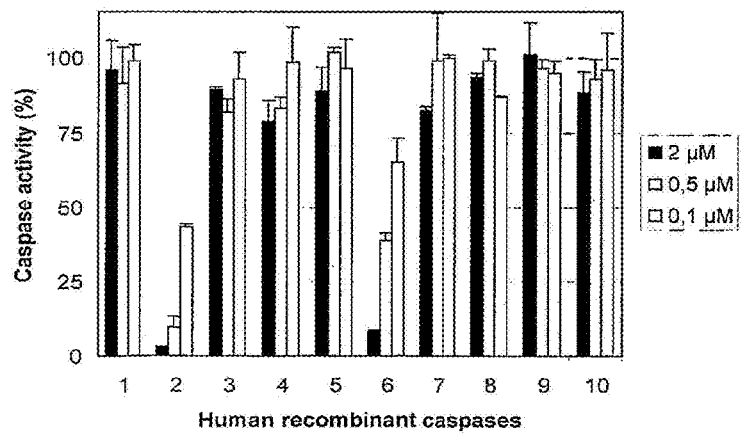
FIG. 13: the inhibition profile of Ac-VDEAD(SEQ ID NO:1-cho, FIG. 14: the inhibition profile of newly designed pentapeptidic inhibitors against recombinant calpain I and II (VDEAD is SEQ ID NO:1, LDEAD is SEQ ID NO:7, VDVAD is SEQ ID NO:9), FIG. 15: the inhibition profile of newly designed pentapeptidic inhibitors against recombinant Granzyme B, FIG. 16: in vitro inhibition of caspase-2 by SEQ8, FIG. 17: SEQ8 provided reduction of infart volume against neonatal ischemic brain injury (48 h) when administered i.p. 1 h post ischemia, FIG. 18: administration by i.v. as otherwise described by FIG. 17 and the accompanying text, FIG. 19: Cresyl-violet staining intensity was partially restored to the level of non-ischemic animal, but without total recovery of the cellular morphology, FIG. 20: shows 40-60% of cells exhibited both nuclear alteration and retained FluoroJade B in the CA1 of ischemic bran.

In addition, it is the first description of dual pentapeptidic-based caspase-2 and caspase-6 inhibitors. These inhibitors exhibit a differential sensitivity against the two caspases, namely caspase-2 and caspase-6. VDEAD(SEQ ID NO:1)-derived compound was able to inhibit both caspases with a nearly similar levels with a nearly similar dose range (FIG. 13). In contrast, LDEAD(SEQ ID NO:7)-derived inhibitor could inhibit caspase-2 at doses that were less active against caspase-6 (FIG. 12).

V/Non Cross-Reactivity Against Others Proteases

V-1/Methodology

Additionally, specificity of newly designed inhibitors was checked against calpains and Granzyme B. Human recombinant calpain I (0.8 U) and rat recombinant calpain II (20 U) (both from Biomol) were pre-incubated 30 min with inhibitors in final 100 μl final assay buffer (50 mM HEPES, pH 7.4, 100 mM NaCl, 0.1% CHAPS, 5 mM CaCl$_2$, 1 mM EDTA, 10% glycerol, 2 mM β-mercaptoethanol) and then mixed with 20 μM of the fluorogenic calpain substrates I or II (Calbiochem), respectively. ALLN and ALLM (1 μM) were internal controls for inhibition. The cleavage of substrates by recombinant enzymes was measured after 2 h at 37° C. on a fluorescence microplate reader by monitoring emission at 460 nm upon excitation at 380 nm for calpain I or emmission at 530 nm upon excitation at 485 nm for calpain II. Human granzyme B (50 U; Biomol) was pre-incubated 10 min with inhibitors in final 100 μl final granzyme assay buffer (Biomol) and then mixed with 400 μM of Ac-IEPD-pNA (Biomol). 3,4 DCIC (1 μM) was used as positive control for inhibition. The cleavage of substrate was measured after 1 h at 37° C. on a spectrophotometer at 360 nm. Ac-IEPD-pNA is DEQ ID NO:29.

V-2/Results and Discussions

LDEAD(SEQ ID NO:7)- and VDEAD(SEQ ID NO:1)-based inhibitors (2 μM) were not strong inhibitors for other cysteine proteases calpain I/II (FIG. 14). LDEAD(SEQ ID NO:7)- and VDEAD(SEQ ID NO:1)-based inhibitors (2 μM) were not strong inhibitors for other protease, granzyme B (FIG. 15).

VI/Caspase Inhibition Reduce Perinatal Ischemic Injury

VI-1/Methodology

Newborn Wistar rats (dam plus 9 pups per litter) were obtained from Janvier (Le Genest-St-Isle, France) when the pups were 3-4 days of age. The pups were housed with their dam under a 12:12 h light-dark cycle with food and water freely available. Animal experimentation was conducted according to the French and European Community guidelines for the care and use of experimental animals. Rat pups were anesthetized with an intraperitoneal injection of chloral hydrate (350 mg/kg). Ischemia was performed in 7 day-old rats (17-21 g), as previously described (Renolleau et al., 1998). Anesthetized rats were positioned on their back and a median incision was made in the neck to expose the left common carotid artery. Rats were then placed on the right side and an oblique skin incision was made between the ear and the eye. After excision of the temporal muscle, the cranial bone was removed from the frontal suture to a level below the zygomatic arch. Then, the left middle cerebral artery, exposed just after its appearance over the rhinal fissure, was coagulated at the inferior level of the cerebral vein. After this procedure, a clip was placed to occlude the left common carotid artery. Rats were then placed in an incubator to avoid hypothermia. After 50 min, the clip was removed. Carotid blood flow restoration was verified with the aid of a microscope. Neck and cranial skin incisions were then closed. During the surgical procedure, body temperature was maintained at 37-38° C. Pups were transferred in an incubator (32° C.) until recovery then after to their dams.

Compound was administered intraperitoneally or intraveinously at 1 h after ischemia (corresponding to the reperfusion). Control animals received an equivalent volume of vehicle required to solubilize the pentapeptidic caspase inhibitor. Rats were killed 48 hours after reperfusion and brains were removed. The infarct lesion (pale zone) was visually scored by an observer blinded to the treatment of animals. Brains without a clear ischemic pale zone were observed under a magnifying glass. Those exhibiting no clear MCA (middle cerebral artery) occlusion were discarded.

Sections from anterior striatum to posterior hippocampus (corresponding to plates 9 to 27 in Paxinos' rat brain atlas) were selected, taken at equally spaced 0.5-mm intervals. The lesion areas were measured on cresyl violet-stained sections using an image analyzer, and the distances between respective coronal sections were used to calculate the infarct volume.

VI-2/Results and Discussions

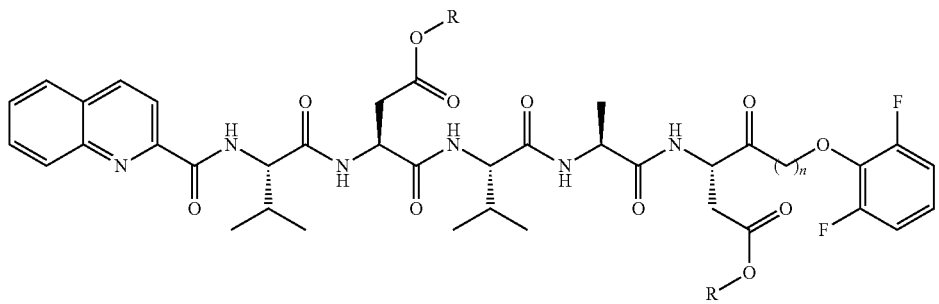

With R=H, Methyl, alkyl or aryl; n=0, 1

2-Quinolinylcarbonyl-L-Valinyl-L-Aspartyl (methyl ester)-L-Vanilyl-L-Alaninyl-L-Aspartyl (methyl ester) 2,6-difluorophenyl ester=SEQ 8 (SEQ ID NO: 9)

The specificity of SEQ8, a newly designed pentapeptidic-inhibitor was tested against recombinant caspase-2. In vitro VDVAD(SEQ ID NO:9)-AMC cleavage by caspase-2 is blocked by SEQ8, as efficiently as commercially available caspase-2 reversible (Ac-VDVAD(SEQ ID NO:9)-Cho) or irreversible (Z-VDVAD(SEQ ID NO:9)-FMK) inhibitors (FIG. 16), but not the caspase-9 inhibitor, z-LEHD-fmk. (SEQ ID NO:27)

Figure 17:
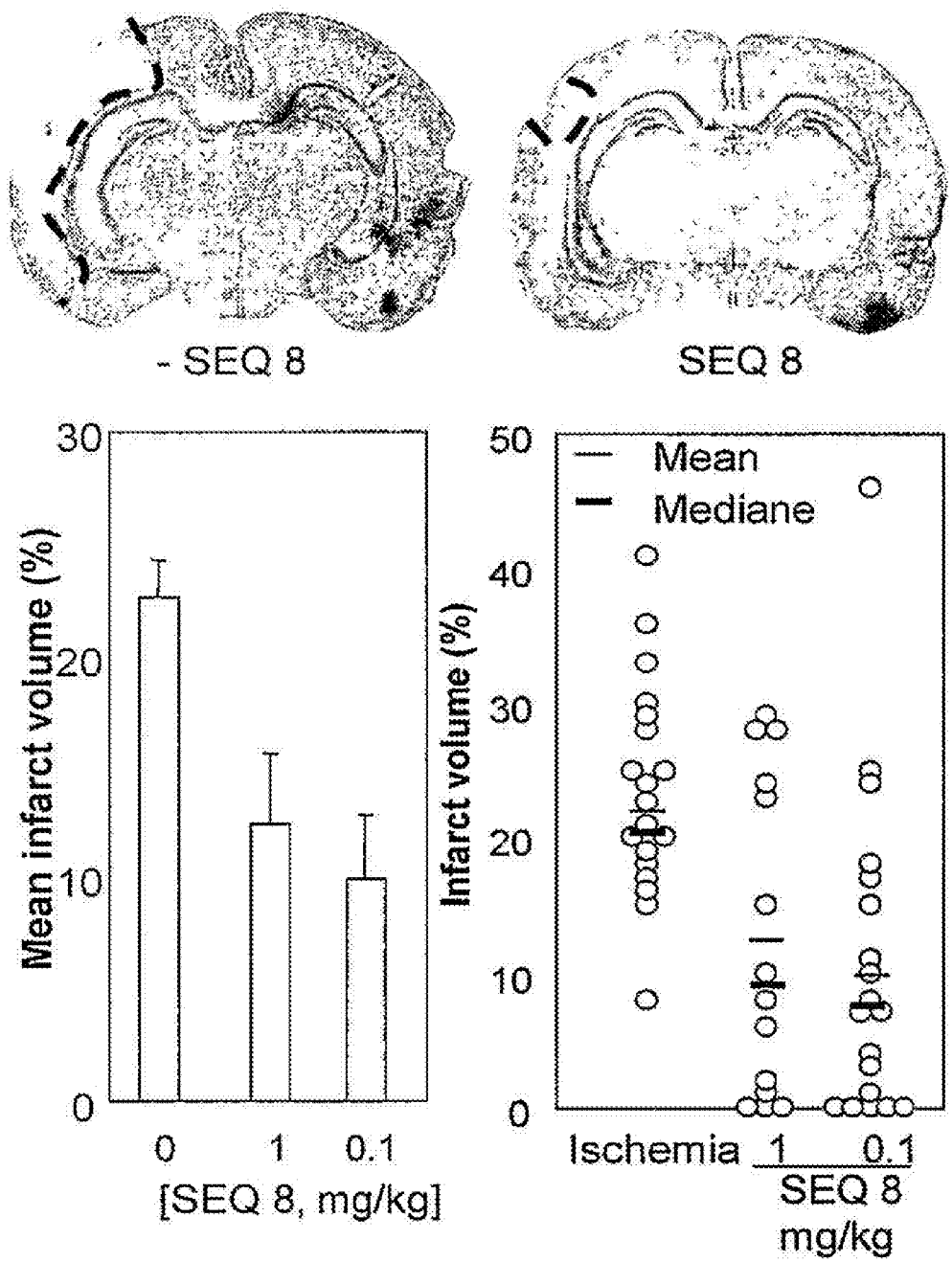
Figure 18:
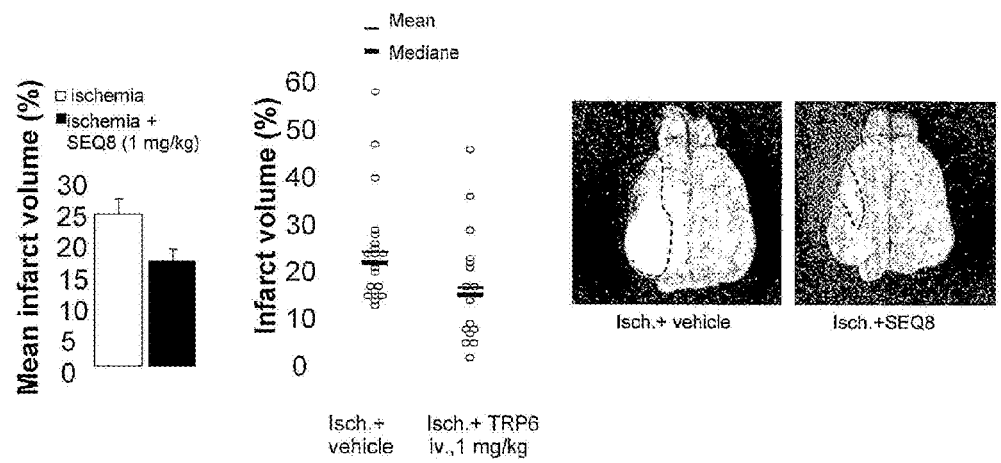

SEQ8 was then tested in an acute model of hypoxic-ischemic injury in the developing brain, in which cell death occurred by apoptosis rather than necrosis. In this transient unilateral focal ischemia model, rat pups underwent permanent left middle cerebral artery occlusion in association with transient occlusion of the left common carotid artery with reperfusion. Neuroprotective effect of SEQ8 was then examined when administrated in this perinatal ischemic model. One dose of SEQ8 (0.1 or 1 mg/kg) or vehicle was administrated i.p. (FIG. 17) or i.v. (FIG. 18) 1 h after the ischemic onset. Brains were then analyzed 48 hours later, a time point at which the infarct was stabilized without significant oedema (no more than 1.5%). Ischemic infarct volume represents a approximately 22-25% damage in the lesioned ipsilateral hemisphere. A single dose of SEQ8 (0.1 or 1 mg/kg) given by i.p. 1 h post-ischemia, significantly reduced the infarct volume by 44-53% (FIG. 17). On the studied animals, more than 50% displayed a partially or very marked reduced infarct (see mediane in histograms and cresyl-violet stained sections). In addition, a single dose of SEQ8 (1 mg/kg) also significantly reduced (by at least 30%) infart volume when given 1 h post-ischemia (FIG. 18). On the studied animals, near 50% displayed a partially or very marked reduced infarct (see mediane in histograms and pale dotted area on freshly extracted brains). To conclude, our data demonstrate that new caspase-2 inhibitors provide strong neuroprotection against neonatal ischemic brain injury.

VII/Caspase Inhibition Reduce Adult Ischemic Injury

VII-1/Methodology

Global cerebral ischemia was induced by four-vessel occlusion (4VO) according a Pulsinelli's derived method (Pulsinelli and Buchman, 1988) in young-adult rats (males Wistar aged of 10-12 weeks, 320 g+/−10 g; Janvier). The first day, head of anesthetised rats was positionned in stereotaxic ear bars and tilted down at approximatively 30° to the horizontal. After a midline incision at the level of cervical spine, both vertebral arteries were exposed under microscope and then coagulated by electocautery needle through the alar foramina at the level of first cervical vertebra. Both common carotides were then exposed 24 h later and clamped for 20-30 min (rats fell in the coma when electrocautherisation of both vertebral arteries have been well performed). Carotid arteries were then declamped to allow blood flow reperfusion. Vehicle and SEQ8 were administrated at the level of the left cerebral ventricule in the first fifth minutes of ischemia (carotides occlusion). Rats were let in their cage with waer et food ad libitum.

The selective loss of vulnerable cells and SEQ8's effects have been evaluated at 72 h. Rats were sacrificed and brain fixed by trans-cardiac perfusion with paraformaldehyde. Frontal brain slices (25 µm) were strained by Cresyl-Violet or co-stained by Hoechst 33342 and Fluorojade B to assess cell death in the hippocampus and in the cortex. Cresyl-Violet is a pink-red dye that labels cytoplasmic body Nissl (endoplasmic reticulum structures) and nuclei in living cells thus resulting in pale or absence of staining in dying cells. Fluoro JadeB (green fluorescence) intake is possible only in cells which have permeable plasma membrane, thus more characteristic of dying cells. Hoechst 33342 (blue fluorescence) label nuclei all cells and allows to appreciate nuclear morphology changes during cell death. Cells are counted in three successive slices at such levels in the hippocampus (CA1) in the left brain hemisphere. Cresyl-Violet stained slices were observed under white light. Both Fluoro Jade B and Hoechst stained slices were observed under a Leica DMIRB inverted fluorescence microscope equipped with ×40 objective and LEICA IM1000/Qfluorobase software (BP 340-80 excitation filter combined with LP 425 emission filter for Hoechst; BP 480/40 excitation filter combined with BP 515-560 emission filter for Fluoro Jade B).

VII-1/Results and Discussion

Figure 19:
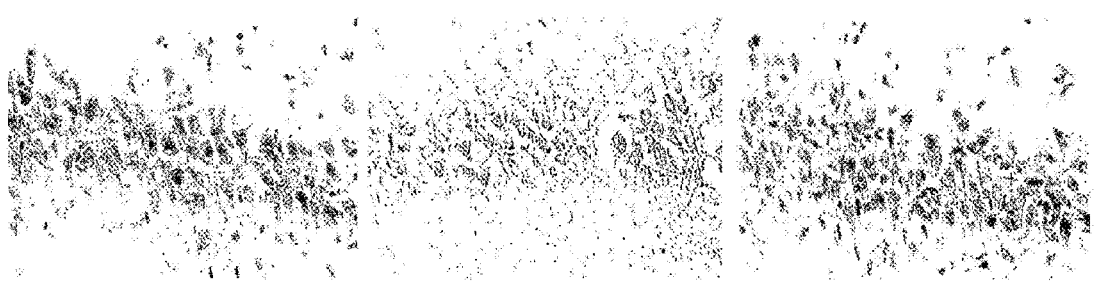
Figure 20:
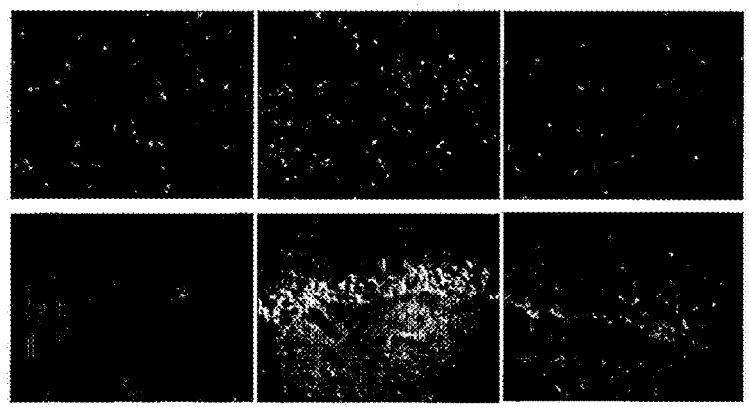

Cell death occurs at the level of CA1 in the hippocampus of 72 h post-ischemic adult rats: 90-100% of cells have lost their Cresyl-violet staining and have abnormal cellular morphology (FIG. 19), 40-60% exhibited both nuclear alteration and retained FluoroJade B in the CA1 of ischemic brain (FIG. 20).

The cytoprotective effects of SEQ8 the level of CA1 was investigated in 72 h post-ischemic brains following, single i.c.v. 60 ng SEQ8 administration. In sharp contrast to ischemic rats, SEQ8's treated animals have less abnormal nuclei (nuclei were bigger and less retracted) and few cells incorporated Fluorojade B (between 10-20% instead of 50-60%) (FIG. 20). Thus colored slices looked like strongly to non-ischemic'ones. Moreover Cresyl-violet staining intensity was partially restored to the level of non-ischemic animal, but without total recovery of the cellular morphology (FIG. 19).

Quantitation of cell death at 72 h post-ischemia. Cell death in the hippocampus (CA1, CA3, DG) and cortex (COR) at 72 h post-ischemia in adult rats. Global and transient cerebral ischemia was induced by 4 vessels occlusion ((4VO; n=5). Rats were treated (icy) with DMSO (here, 7.255%; 0.7255% not shown) (n=5). A: Quantitation of Cresyl-Violet positives cells at the level of injection of DMSO or TRP6 (1), 650 μm after (2) or 780 μm after (3). B: Quantitation of abnormal nuclei assessed by Hoechst staining in the hippocampus (CA1$_{a,b,c}$, CA3, DG) and cortex (COR) of ischemic and non-ischemic brains. C: Quantitation of Fluor® Jade B positive cells in the hippocampus (CA1$_{a,b,c}$, CA3, DG) and cortex (COR) of ischemic and non-ischemic brains.

We claim:

1. A peptide consisting of:

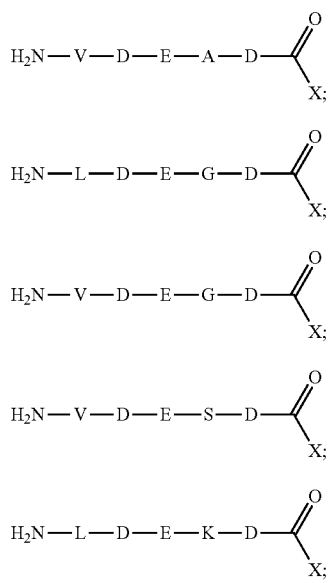

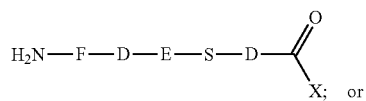

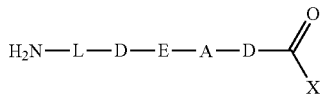

wherein
X is H.

2. A pharmaceutical composition comprising a therapeutically effective amount of at least one peptide of claim 1 in association with a pharmaceutically acceptable carrier.

3. The pharmaceutical composition according to claim 2, wherein said at least one peptide is present in a dose amount of from $10^{-9}$ mg/kg to 100 g/kg of a patient.

4. The pharmaceutical composition according to claim 3, wherein said at least one peptide is present in a dose amount of from 0.1 to 10 mg/kg.

* * * * *